(12) United States Patent
Madden

(10) Patent No.: US 12,171,868 B2
(45) Date of Patent: Dec. 24, 2024

(54) INTRANASAL OLANZAPINE FORMULATIONS AND METHODS OF THEIR USE

(71) Applicant: Neurelis, Inc., San Diego, CA (US)

(72) Inventor: Stuart Madden, San Diego, CA (US)

(73) Assignee: Neurelis, Inc., San Diego, CA (US)

( * ) Notice: Subject to any disclaimer, the term of this patent is extended or adjusted under 35 U.S.C. 154(b) by 0 days.

(21) Appl. No.: 18/125,940

(22) Filed: Mar. 24, 2023

(65) Prior Publication Data

US 2023/0301903 A1 Sep. 28, 2023

Related U.S. Application Data

(60) Provisional application No. 63/323,592, filed on Mar. 25, 2022.

(51) Int. Cl.
| | | |
|---|---|---|
| *A61K 9/00* | (2006.01) | |
| *A61K 31/5513* | (2006.01) | |
| *A61K 47/10* | (2017.01) | |
| *A61K 47/18* | (2017.01) | |
| *A61K 47/26* | (2006.01) | |

(52) U.S. Cl.
CPC ........ *A61K 9/0043* (2013.01); *A61K 31/5513* (2013.01); *A61K 47/10* (2013.01); *A61K 47/18* (2013.01); *A61K 47/26* (2013.01)

(58) Field of Classification Search
CPC .............................. A61K 9/0043; A61K 47/10
See application file for complete search history.

(56) References Cited

U.S. PATENT DOCUMENTS

| 8,106,188 B2 | 1/2012 | Ray et al. | |
|---|---|---|---|
| 2005/0063940 A1 * | 3/2005 | Gizurarson | A61K 47/14 424/78.38 |
| 2006/0287299 A1 | 12/2006 | Sheldon | |
| 2019/0240150 A1 * | 8/2019 | Hoekman | A61K 31/5513 |

FOREIGN PATENT DOCUMENTS

| WO | WO-2021198115 A1 * | 10/2021 | ........... A61K 31/167 |
|---|---|---|---|
| WO | 2023183557 A1 | 9/2023 | |

OTHER PUBLICATIONS

Zareifopoulos N, Panayiotakopoulos G. Treatment Options for Acute Agitation in Psychiatric Patients: Theoretical and Empirical Evidence. Cureus. Nov. 14, 2019;11(11) (Year: 2019).*
Katharya, Anil & Choudhary, Ratendra & Sharma, Rajiv & Singh, Yogendra & Teotia, U.V.S. (2013). Development and Optimization of Solid Dispersion of Olanzapine in Poly Ethylene Glycol by D-Optimal Response Surface Factorial Design. International Journal of PharmTech Research. 5. 700-710 (Year: 2013).*
Vetter A, Augustijns P, Bernkop-Schnurch A. Solubilizing agents in nasal formulations and their effect on ciliary beat frequency. Toxicol In Vitro. Feb. 2012;26(1) (Year: 2012).*
Korni et al., Nov. 2018 Indian Journal of Pharmaceutical Sciences 80(6) (Year: 2018).*
Ghayor C, Gjoksi B, Dong J, Siegenthaler B, Caflisch A, Weber FE. N,N Dimethylacetamide a drug excipient that acts as bromodomain ligand for osteoporosis treatment. Sci Rep. Feb. 8, 2017;7:42108 (Year: 2017).*
Vetter A, Augustijns P, Bernkop-Schnürch A. Solubilizing agents in nasal formulations and their effect on ciliary beat frequency. Toxicol In Vitro. Feb. 2012;26(1) (Year: 2012) (Year: 2012).*
Korni et al., Nov. 2018 Indian Journal of Pharmaceutical Sciences 80(6) (Year: 2018) (Year: 2018).*
Ghayor C, Gjoksi B, Dong J, Siegenthaler B, Caflisch A, Weber FE. N,N Dimethylacetamide a drug excipient that acts as bromodomain ligand for osteoporosis treatment. Sci Rep. Feb. 8, 2017;7:42108 (Year: 2017) (Year: 2017).*
Drug Label—Updated Apr. 27, 2020 https://dailymed.nlm.nih.gov/dailymed/lookup.cfm?setid=1e9666ef-4271-4834-8496-ccb3125d83db (Year: 2020).*
International Search Report and Written Opinion for International Application PCT/US2023/016204 dated Aug. 18, 2023.

* cited by examiner

*Primary Examiner* — Clinton A Brooks
*Assistant Examiner* — Izabela Schmidt
(74) *Attorney, Agent, or Firm* — DLA Piper LLP (US)

(57) ABSTRACT

Compositions for intranasal delivery of olanzapine and methods for their use to treat various symptoms of schizophrenia, schizoaffective disorder, and bipolar disorder, such as acute agitation, mania, and mixed episodes. Intranasal olanzapine compositions comprise dodecyl maltoside to improve bioavailability of olanzapine and is administered via nasal mucosa to avoid direct systemic administration.

30 Claims, 4 Drawing Sheets

INTRANASAL OLANZAPINE FORMULATIONS AND METHODS OF THEIR USE

CROSS-REFERENCE TO RELATED APPLICATIONS

This application claims priority to U.S. Provisional Application No. 63/323,592 filed Mar. 25, 2022 which is hereby incorporated by reference in its entirety.

FIELD

The present disclosure relates generally to compositions comprising olanzapine and an alkyl maltoside, suitable for intranasal administration and effective to treat acute agitation associated with schizophrenia, schizoaffective disorder, and bipolar disorder and maintenance treatment of schizophrenia, schizoaffective disorder, bipolar disorder, and treatment-resistant depression.

BACKGROUND

Olanzapine is an atypical antipsychotic that is approved for the treatment of schizophrenia, schizoaffective disorder and bipolar disorder. Individuals affected by these conditions are vulnerable to episodes of agitation, which can range from mild to severe, fluctuate rapidly and escalate to aggressive behavior in a short period of time; symptoms include motor restlessness, increased response to external stimuli, irritability and unsuitable speech and may develop into physical aggression typically directed towards family members and medical personnel.

Olanzapine intramuscular (IM) injection is typically used to treat acute agitation episodes because of a shorter time to peak concentration than oral or oral disintegrating tablets. Rapid onset of action is highly desirable, and traditionally, intramuscular injection of olanzapine has been the fast-acting route of administration approved in the United States. However, olanzapine intramuscular injections require reconstitution prior to administration, require administration by a Health Care Provider (HCP), may require restraint, is invasive, and can be painful. In addition, in less cooperative patients, it poses a risk for needle stick injury to health care workers, caregivers, and patients.

What is needed is a non-invasive, convenient, needle-free method of olanzapine delivery that can be utilized in acutely agitated patients without the aid of an HCP that has a rapid onset of therapeutic effect. Such a method may also be beneficial in providing therapeutic effect to subjects suffering from schizophrenia, schizoaffective disorder, bipolar disorder, and/or treatment-resistant depression via a form more conveniently administered than the current oral forms available.

SUMMARY

The present disclosure provides, in one embodiment, a composition comprising: about 1% w/v to about 15% w/v of olanzapine or a pharmaceutically acceptable salt thereof about 0.1% w/v to about 1% w/v of dodecyl maltoside; about 30% w/v to about 40% w/v of N,N-dimethylacetamide; and about 40% w/v to about 70% w/v of polyethylene glycol, wherein the composition is a non-aqueous solution comprising less than about 3% w/v of water.

In some embodiments, the composition comprises about 2.5% w/v to about 12% w/v of the olanzapine or a pharmaceutically acceptable salt thereof. In some embodiments, the composition comprises about 0.20% w/v to about 0.50% w/v of the dodecyl maltoside. In some embodiments, the composition comprises about 34% w/v to about 38% w/v of the N,N-dimethylacetamide. In some embodiments, the polyethylene glycol has an average molecular weight of about 200 Da to about 1000 Da. In some embodiments, the polyethylene glycol has an average molecular weight of about 600 Da. In some embodiments, the composition comprises about 44% w/v to about 66% w/v of the polyethylene glycol. In some embodiments, the amount of olanzapine is about 1 mg to about 15 mg or a pharmaceutically acceptable salt thereof. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. In some embodiments, the composition comprises about 2.5% w/v to about 12% w/v of the olanzapine or a pharmaceutically acceptable salt thereof, about 0.20% w/v to about 0.50% w/v of the dodecyl maltoside, about 34% w/v to about 38% w/v of the N,N-dimethylacetamide, and about 44% w/v to about 66% w/v of the polyethylene glycol. In some embodiments, the composition comprises less than about 1% w/v of water. In some embodiments, the composition comprises less than 0.1% w/v of water.

Some embodiments are directed to a single-use spray device comprising a composition according to present disclosure, configured to discharge a volume of the composition that corresponds to 2.5 mg olanzapine to 15 mg of olanzapine upon actuation of the device.

Some embodiments are directed to a metered-multiple use spray device comprising a composition according to the present disclosure, configured to discharge a volume of the composition that corresponds to 2.5 mg olanzapine to 15 mg of olanzapine upon actuation of the device.

Some embodiments are directed to methods of treating acute agitation associated with one or more of schizophrenia, schizoaffective disorder, and bipolar disorder in a subject in need thereof comprising intranasally administering a composition comprising about 1% w/v to about 15% w/v of olanzapine or a pharmaceutically acceptable salt thereof, about 0.1% w/v to about 1% w/v dodecyl maltoside, about 30% w/v to about 40% w/v N,N-dimethylacetamide, and about 40% w/v to about 70 mg of polyethylene glycol to a nasal mucosal membrane of the subject, wherein the composition is a non-aqueous solution comprising less than about 3% w/v of water.

Some embodiments are directed to methods of treating depression associated with bipolar disorder comprising intranasally administering a composition comprising about 1% w/v to about 15% w/v of olanzapine or pharmaceutically acceptable salt thereof, about 0.1% w/v to about 1% w/v dodecyl maltoside, about 30% w/v to about 40% w/v N,N-dimethylacetamide, and about 40% w/v to about 70% w/v of polyethylene glycol to a nasal mucosal membrane of the subject, wherein the composition is a non-aqueous solution comprising less than about 3% w/v of water.

Some embodiments are directed to methods of treating mania associated with bipolar disorder comprising intranasally administering a composition comprising about 1% w/v to about 15% w/v of olanzapine or a pharmaceutically acceptable salt, about 0.1% w/v to about 1% w/v dodecyl maltoside, about 30% w/v to about 40% w/v N,N-dimethylacetamide, and about 40% w/v to about 70% w/v of polyethylene glycol to a nasal mucosal membrane of the subject, wherein the composition is a non-aqueous solution comprising less than about 3% w/v of water.

Some embodiments are directed to methods of treating a mixed episode associated with bipolar disorder comprising intranasally administering a composition comprising about 1% w/v to about 15% w/v of olanzapine or a pharmaceutically acceptable salt thereof, about 0.1% w/v to about 1% w/v dodecyl maltoside, about 30% w/v to about 40% w/v N,N-dimethylacetamide, and about 40% w/v to about 70% w/v of polyethylene glycol to a nasal mucosal membrane of the subject, wherein the composition is a non-aqueous solution comprising less than about 3% w/v of water.

In some embodiments, the compositions for use in the methods described herein comprise about 1 mg to about 15 mg of the olanzapine or a pharmaceutically acceptable salt thereof. In some embodiments, the compositions for use in the methods described herein comprise about 2.5 mg to about 10 mg of the olanzapine or a pharmaceutically acceptable salt thereof. In some embodiments, the compositions for use in the methods described herein comprises about 0.20% w/v to about 0.50% w/v of the dodecyl maltoside. In some embodiments, the composition for use in the methods described herein comprise about 34% w/v to about 38% w/v of the N,N-dimethylacetamide. In some embodiments, the polyethylene glycol has an average molecular weight of about 200 Da to about 1000 Da. In some embodiments, the compositions for use in the methods described herein comprise about 44% w/v to about 66% w/v of the polyethylene glycol. In some embodiments, the compositions for use in the methods described herein comprise about 2.5 mg to about 12 mg of the olanzapine or a pharmaceutically acceptable salt thereof, about 0.20% w/v to about 0.50% w/v dodecyl maltoside, about 34% w/v to about 38% w/v of the N,N-dimethylacetamide, and about 44% w/v to about 66% w/v of polyethylene glycol.

In some embodiments, the severity of the acute agitation in the subject is reduced within about 20 minutes after administration. In some embodiments compositions for use in the methods disclosed herein are provided in a pre-primed single use dosing device containing about 75 µL to about 200 µL of the composition. In some embodiments, said administering comprises administering about 75 µL to about 200 µL of the composition to each nostril of the subject. In some embodiments, the depression, mania, or mixed episodes manifest as recurring episodes and wherein one or more of the frequency, length, and severity of the recurring episodes is reduced. In some embodiments, the compositions for use in the methods disclosed herein comprise less than 1% w/v of water.

DETAILED DESCRIPTION

Figure 1:
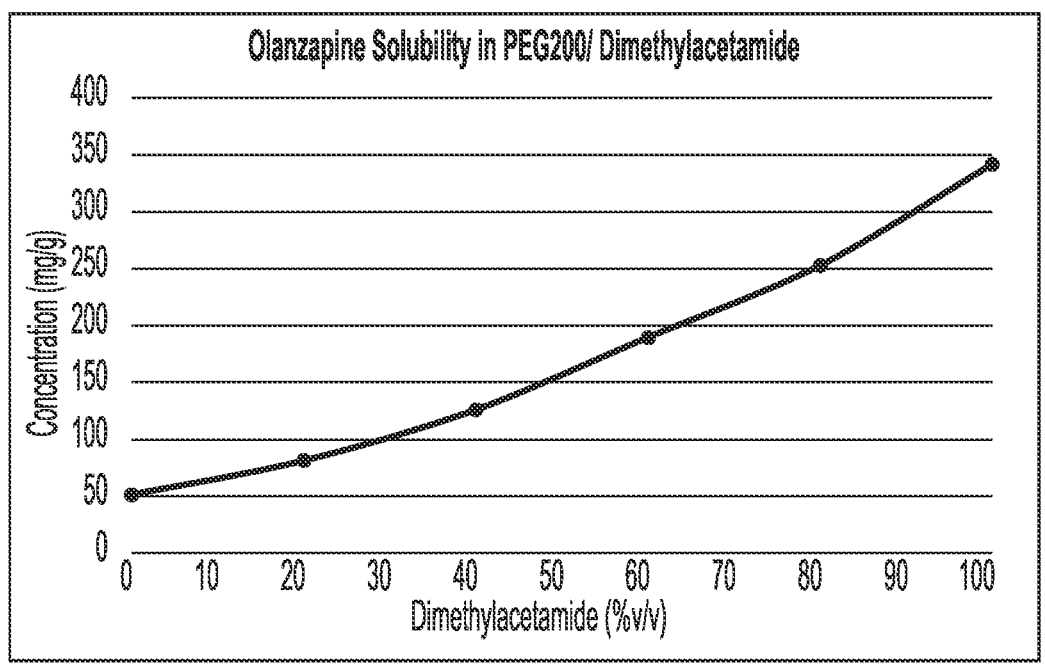
FIG. 1 depicts saturated Solubility for dimethylacetamide/PEG 200 binary solvent system.

Before the present compositions and methods are described, it is to be understood that various aspects of intranasal olanzapine compositions and methods of their use are disclosed herein. Unless indicated otherwise, all technical and scientific terms used herein have the meaning commonly understood by one of ordinary skill in the art. It is also to be understood that the terminology used in the description is for the purpose of describing the particular aspects or embodiments only and is not intended to limit the scope. The disclosed intranasal olanzapine compositions, method of their manufacture, and methods of their use are not strictly limited to the particular compositions, processes, or methods described, as these can vary to an extent one of skill in the art will recognize without diverging from the benefits and advantages imparted by the compositions and methods. Though one of skill in the art will readily recognize obvious variations and substitutions that may be made to accomplish the same result through equivalent means or function, for the purpose of describing the various aspects and embodiments of intranasal olanzapine compositions, methods of their manufacture, and methods of their use, preferred compositions and methods are now described.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable sub combination.

The compositions disclosed herein are suitable for administration to the nasal cavity. As such, the phrases "intranasal solution," "intranasal composition," and "intranasal formulation" are used interchangeably to mean a composition suitable for administration to the nasal mucosal membranes which line the nasal cavity.

The intranasal olanzapine compositions disclosed herein may be used to treat various symptoms of schizophrenia, schizoaffective disorder, bipolar disorder, and depression, particularly treatment-resistant depression.

Schizophrenia is a serious mental illness that affects how a person thinks, feels, and behaves and involves a breakdown in the relationship between these aspects of a person's life, leading to inappropriate actions and feelings, withdrawal from reality and personal relationships, and a sense of mental fragmentation. Generally, schizophrenia develops in at least three stages: the prodromal phase, the first episode, and the chronic phase. There is also heterogeneity of individuals at all stages of the disorder, with some individuals considered ultra-high risk, clinical-high risk, or at-risk for the onset of psychosis (Fusar-Poli et al., "The Psychosis High-Risk State: A Comprehensive State-of-the-Art Review," JAMA Psychiatry 70:107-120 (2013), which is hereby incorporated by reference in its entirety). The methods described herein are suitable for treating a subject in any stage of schizophrenia, and at any risk level of psychosis.

Schizoaffective disorder is a combination of symptoms of schizophrenia and mood disorder, such as depression or bipolar disorder. Symptoms may occur at the same time or at different times. Cycles of severe symptoms are often followed by periods of improvement. Symptoms may include delusions, hallucinations, depressed episodes, and manic periods of high energy. There are two types of schizoaffective disorder—bipolar type which is characterized by episodes of mania and sometimes major depression and depressive type which is characterized by only major depressive episodes.

Bipolar disorder, sometimes known as manic depression, is a mental illness that brings severe high (mania) and low (depression) moods and changes in sleep, energy, thinking, and behavior. People who have bipolar disorder can have periods ("episodes") in which they feel overly happy and energized and other periods of feeling very sad, hopeless, and sluggish. Episodes of mood swings may occur rarely or multiple times a year. Bipolar I disorder is characterized by at least one manic episode that may be preceded or followed by hypomanic (a milder form of mania) or depressive episodes. Bipolar II disorder is characterized by at least one major depressive episode and at least one hypomanic episode but a lack of a manic episode.

Mania and hypomania are two distinct types of episodes, but they have the same symptoms. Mania is more severe than hypomania and causes more noticeable problems at work, school and social activities, as well as relationship difficulties. Mania may also trigger a break from reality (psychosis) and require hospitalization. A major depressive episode includes symptoms that are severe enough to cause noticeable difficulty in day-to-day activities, such as work, school, social activities or relationships. Mixed episodes are defined by symptoms of mania and depression that occur at the same time or in rapid sequence without recovery in between.

Generally, bipolar disorders are progressive conditions which develop in at least three stages: the prodromal phase, the symptomatic phase, and the residual phase (Kapczinski et al., "Clinical Implications of a Staging Model for Bipolar Disorders," Expert Rev Neurother 9:957-966 (2009), and McNamara et al., "Preventative Strategies for Early-Onset Bipolar Disorder: Towards a Clinical Staging Model," CNS Drugs 24:983-996 (2010), which are hereby incorporated by reference in their entirety). The methods described herein are suitable for treating subjects having any of the aforementioned bipolar disorders and subjects in any stage of a particular bipolar disorder.

Acute agitation is defined as excessive motor activity associated with a feeling of inner tension and can be associated with schizophrenia, schizoaffective disorder, and bipolar disorder (as well as many other psychiatric disorders).

Treatment-resistant depression (TRD) typically refers to inadequate response to at least one antidepressant trial of adequate doses and duration.

The terms "treat", "treated", or "treating" as used herein refer to both therapeutic treatment and prophylactic or preventative measures, wherein the object is to protect against (partially or wholly) or slow down (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this disclosure, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects. Treatment also includes prolonging survival as compared to expected survival if not receiving treatment. As used herein, "treating" and other grammatical forms thereof (e.g., treat, treatment) may also improve symptoms of a disease or condition, such as schizophrenia, schizoaffective disorder, bipolar disease, or TRD. Improvement may include reducing the frequency, length, or severity of one or more symptoms. The physiological cause of many psychiatric conditions or disease, including schizophrenia, schizoaffective disorder, bipolar disease, and TRD are not entirely understood but are thought to arise from abnormal biochemical signaling in the brain. Therefore, the compositions and methods disclosed herein may temporarily treat symptoms caused by the abnormal biochemical signaling or alter the biochemical signaling on a temporary basis but may not adequately treat the root cause of the abnormal signaling. In this way, a subject being "treated" with the compositions and by the methods described herein will experience improved symptoms of their disease or condition but a maintenance therapy, or prolonged administration regimen, may be necessary to maintain said improved symptoms. In many cases, the prolonged administration regimen may last months, years, or even for the remainder of a subject's life.

In any embodiment, the methods and compositions disclosed herein may comprise the recited steps and components. As used here, "comprise" is open language used to recite steps or components that are included in the recited method or composition but to indicate that other elements may also be included, even though said elements are not explicitly recited. In any embodiment, the methods and compositions disclosed herein may consist essentially of the recited steps and components. As used here, "consist essentially of" is used to recite steps or components that are included in the recited method or composition and to indicate that other elements may also be included but said other elements would not materially affect the properties of the composition or the results of the method. In any embodiment, the methods and compositions disclosed herein may consist of the recited steps and components. As used here, "consist of" is closed language used to recite steps or components that are included in the recited method or composition and that no other elements are included other than those explicitly recited. Any use of the term comprise, comprises or comprising may be replaced with "consisting essentially of" or "consisting of."

The singular forms "a", "an", and "the" include plural reference unless the context clearly dictates otherwise. Thus, for example, reference to a "cell" is a reference to one or more cells and equivalents thereof known to those skilled in the art, and so forth.

The term "about" as used herein, means plus or minus 1% of a given value. For example, "about 50%" means in the range of 49.5%-50.5%. The term "about" as used herein, means plus or minus 2% of a given value. For example, "about 50%" means in the range of 49%-51%. The term "about" as used herein, means plus or minus 3% of a given value. For example, "about 50%" means in the range of 48.5-51.5%. The term "about" as used herein, means plus or minus 4% of a given value. For example, "about 50%" means in the range of 48%-52%. The term "about" as used herein, means plus or minus 5% of a given value. For example, "about 50%" means in the range of 47.5-52.5%. The term "about" as used herein, means plus or minus 6% of a given value. For example, "about 50%" means in the range of 47%-53%. The term "about" as used herein, means plus or minus 7% of a given value. For example, "about 50%" means in the range of 46.5%-53.5%. The term "about" as used herein, means plus or minus 8% of a given value. For example, "about 50%" means in the range of 46%-54%. The term "about" as used herein, means plus or minus 9% of a given value. For example, "about 50%" means in the range of 45.5%-54.5%. The term "about" as used herein, means plus or minus 10% of a given value. For example, "about 50%" means in the range of 45-55%. The term "about" as used herein, can also mean plus or minus 5% of a given value. For example, "about 50%" means in the range of 47.5%-52.5%. The term "about" as used herein, can also mean plus or minus 15% of a given value. For example, "about 50%" means in the range of 42.5-57.5%. The term "about" as used herein, can also mean plus or minus 20% of a given value. For example, "about 50%" means in the range of 40%-60%.

As used herein, the term "subject" and "patient" expressly includes human and non-human mammalian subjects. The term "non-human mammal" as used herein extends to, but is not restricted to, household pets and domesticated animals. Non-limiting examples of such animals include primates, cattle, sheep, ferrets, mice, rats, swine, camels, horses, rabbits, goats, dogs and cats.

The term "effective amount" as used herein, refers to an amount that results in measurable inhibition of at least one symptom or parameter of a specific disorder or pathological process. For example, an effective amount of olanzapine may be from about 1 mg to about 15 mg.

The terms "therapeutically effective amount" or "effective amount" of a compound or composition of the disclosure as used herein, refers to a predetermined amount which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect or physician observes a change). An effective amount of a compound of the disclosure may broadly range from about 1 mg to about 15 mg of olanzapine. The effect contemplated herein includes both medical therapeutic and/or prophylactic treatment, as appropriate. The specific dose of a compound administered according to this disclosure to obtain therapeutic and/or prophylactic effects will, of course, be determined by the particular circumstances surrounding the case, including, for example, the compound administered, the route of administration, the co-administration of other active ingredients, the condition being treated, the activity of the specific compound employed, the specific composition employed, the age, body weight, general health, sex and diet of the patient; the time of administration, route of administration, and rate of excretion of the specific compound employed and the duration of the treatment. The effective amount administered will be determined by the physician in the light of the foregoing relevant circumstances and the exercise of sound medical judgment. A therapeutically effective amount of a compound of this disclosure is typically an amount such that when it is administered in a physiologically tolerable excipient composition, it is sufficient to achieve an effective systemic concentration or local concentration in the tissue. The total daily dose of the compounds of this disclosure administered to a human or other animal in single or in divided doses can be in amounts, for example, about 1 mg to about 15 mg. Single dose compositions may contain such amounts or submultiples thereof to make up the daily dose. In general, treatment regimens according to the disclosure comprise administration to a patient in need of such treatment will usually include from about 1 mg to about 10 mg, about 1 mg to about 15 mg, about 1 mg to about 30 mg, about 1 mg to about 60 mg, or about 1 mg to about 120 mg a compound according to Formula I, or a pharmaceutically acceptable salt thereof, per day in single or multiple doses.

A therapeutically effective amount of olanzapine may be administered as a therapeutically effective dose of an intranasal olanzapine composition as disclosed herein. A therapeutically effective dose of the intranasal olanzapine composition may be administered in a single volume (e.g., to one nostril of a subject) or in two or more volumes (e.g., a first volume to one nostril and a second volume to the second nostril to result in administration of a therapeutically effective dose). A therapeutically effective dose may comprise 1 mg to about 15 mg of olanzapine or a pharmaceutically acceptable salt thereof. In some embodiments, the intranasal olanzapine composition may further comprise about 0.1 mg to about 1 mg of dodecyl maltoside, about 30 mg to about 40 mg of N, N, dimethylacetamide (DMA), and about 40 mg to about 70 mg of polyethylene glycol ("PEG"). A suitable volume for administration to one or more nostrils of a subject may be about 75 µL, about 100 µL, about 125 µL, about 150 µL, about 200 µL, or any value there between.

Therefore, the intranasal olanzapine compositions and methods of their use as provided herein represent a substantial improvement in the aforementioned treatments, especially in treating acute agitation associated with schizophrenia, schizoaffective disorder and bipolar disorder due to the rapid realization of therapeutic benefit after administration.

Compositions

The present disclosure provides intranasal compositions comprising olanzapine or a pharmaceutically acceptable salt thereof. The intranasal olanzapine compositions are suitable and intended for intranasal administration, as described above. Olanzapine is chemically known as 2-methyl-4-(4-methyl-1-piperazinyl)-10H-thieno[2,3-b] [1,5]benzodiazepine and has a chemical structure of Formula I:

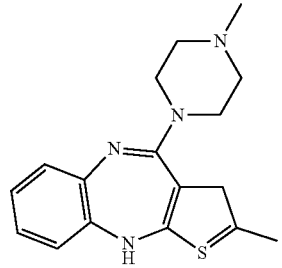

Formula I

Formula I depicts olanzapine in its free base form, however, olanzapine may be present in any intranasal olanzapine composition described herein as a salt form (e.g., dicarboxylic acid salt such as tartrate), a solvate (e.g., hydrate), polymorph, a cocrystal, in a complex or any combination thereof. All recitations of concentrations or amounts of olanzapine refer to the free base form; however, a pharmaceutically acceptable salt thereof, solvate, hydrate, cocrystal, or any combination thereof may be used. One of skill in the art will be able to determine the therapeutically equivalent amount of a pharmaceutically acceptable salt of olanzapine as it compares to an amount of the free base.

The term "pharmaceutically acceptable" as used herein, refers to molecular entities and compositions that are generally regarded as safe and nontoxic. In particular, pharmaceutically acceptable carriers, diluents or other excipients used in the pharmaceutical compositions of this disclosure are physiologically tolerable, compatible with other ingredients, and do not typically produce an allergic or similar untoward reaction (for example, gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The phrase "pharmaceutically acceptable salt(s)", as used herein, includes those salts of compounds of the disclosure that are safe and effective for use in mammals and that possess the desired biological activity. Pharmaceutically acceptable salts include salts of acidic or basic groups present in compounds of the disclosure or in compounds identified pursuant to the methods of the disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Suitable base salts include, but are not limited to, aluminum, calcium, lithium, magnesium, potassium, sodium, zinc, iron and diethanolamine salts. Pharmaceutically acceptable base addition salts are also formed with amines, such as organic amines. Examples of suitable amines are N,N'-dibenzylethylenediamine, chloroprocaine, choline, diethanolamine, dicyclohexylamine, ethylenediamine, N-methylglucamine, and procaine.

A composition for delivering olanzapine intranasally (herein "intranasal olanzapine composition") comprises olanzapine or a pharmaceutically acceptable salt thereof, an alkyl maltoside, N,N-dimethylacetamide (DMA), and polyethylene glycol (PEG). Preferably, the PEG is characterized by an average molecular weight of about 200 Da to less than about 1000 Da, such as about 300 Da to about 800 Da, or about 500 Da to about 700 Da, such as PEG-600. Examples of suitable alkyl maltosides include $C_9$-$C_{14}$ maltosides such as dodecyl maltoside and tetradecyl maltoside, particularly n-dodecyl-β-D-maltoside. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2.

A composition for delivering a therapeutically effective amount of olanzapine intranasally (herein "intranasal olanzapine composition") comprises olanzapine or a pharmaceutically acceptable salt thereof, an alkyl maltoside, N,N-dimethylacetamide (DMA), and polyethylene glycol (PEG). Preferably, the PEG is characterized by an average molecular weight of about 200 Da to less than about 1000 Da, such as about 300 Da to about 800 Da, or about 500 Da to about 700 Da, such as PEG-600. Examples of suitable alkyl maltosides include $C_9$-$C_{14}$ maltosides such as dodecyl maltoside and tetradecyl maltoside, particularly n-dodecyl-β-D-maltoside. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2.

An intranasal olanzapine composition may comprise one or more doses, wherein each dose comprises a therapeutically effective amount of olanzapine (or a pharmaceutically acceptable salt thereof), about 0.1 mg to about 1 mg of dodecyl maltoside, about 30 mg to about 40 mg of DMA, and about 40 mg to about 70 mg of polyethylene glycol. An intranasal olanzapine composition may comprise about 1% w/v to about 15% w/v of olanzapine (or a pharmaceutically acceptable salt thereof), about 0.1% w/v to about 1% w/v of dodecyl maltoside, about 30% w/v to about 40% w/v of DMA, and about 40% w/v to about 70% w/v of polyethylene glycol. In any embodiment, one or more doses of the intranasal olanzapine composition described above may be used to deliver a therapeutically effective amount of olanzapine to a subject in need thereof to treat a disorder, condition, or disease treatable with olanzapine, such as schizophrenia, schizoaffective disorder, bipolar disorder, and TRD.

An intranasal olanzapine composition may comprise one or more doses, wherein each dose comprises about 1 mg to about 15 mg of olanzapine (or a pharmaceutically acceptable salt thereof), about 0.1 mg to about 1 mg of dodecyl maltoside, about 30 mg to about 40 mg of DMA, and about 40 mg to about 70 mg of polyethylene glycol. An intranasal olanzapine composition may comprise about 1% w/v to about 15% w/v of olanzapine (or a pharmaceutically acceptable salt thereof), about 0.1% w/v to about 1% w/v of dodecyl maltoside, about 30% w/v to about 40% w/v of DMA, and about 40% w/v to about 70% w/v of polyethylene glycol. In any embodiment, one or more doses of the intranasal olanzapine composition described above may be used to deliver a therapeutically effective amount of olanzapine to a subject in need thereof to treat a disorder, condition, or disease treatable with olanzapine, such as schizophrenia, schizoaffective disorder, bipolar disorder, and TRD.

In another example, each dose comprise may comprise a therapeutically effective amount of olanzapine or a pharmaceutically acceptable salt thereof, about 0.20 mg to about 0.50 mg of dodecyl maltoside, about 34 mg to about 38 mg of DMA, and about 44 mg to about 66 mg of polyethylene glycol. An intranasal olanzapine composition may therefore comprise about 2.5% w/v to about 12% w/v of olanzapine (or a pharmaceutically acceptable salt thereof), about 0.20% w/v to about 0.50% w/v of dodecyl maltoside, about 34% w/v to about 38% w/v of DMA, and about 44% w/v to about 66% w/v of polyethylene glycol. In any embodiment, one or more doses of the intranasal olanzapine composition described above may be used to deliver a therapeutically effective amount of olanzapine to a subject in need thereof to treat a disorder, condition, or disease treatable with olanzapine, such as schizophrenia, schizoaffective disorder, bipolar disorder, and TRD.

In another example, each dose comprise may comprise about 2.5 mg to about 12 mg of olanzapine or a pharmaceutically acceptable salt thereof, about 0.20 mg to about 0.50 mg of dodecyl maltoside, about 34 mg to about 38 mg of DMA, and about 44 mg to about 66 mg of polyethylene glycol. An intranasal olanzapine composition may therefore comprise about 2.5% w/v to about 12% w/v of olanzapine (or a pharmaceutically acceptable salt thereof), about 0.20% w/v to about 0.50% w/v of dodecyl maltoside, about 34% w/v to about 38% w/v of DMA, and about 44% w/v to about 66% w/v of polyethylene glycol. In any embodiment, one or more doses of the intranasal olanzapine composition described above may be used to deliver a therapeutically effective amount of olanzapine to a subject in need thereof to treat a disorder, condition, or disease treatable with olanzapine, such as schizophrenia, schizoaffective disorder, bipolar disorder, and TRD.

In another example, each dose comprise may comprise a therapeutically effective amount of olanzapine or a pharmaceutically acceptable salt thereof, about 0.25 mg to about 0.50 mg of dodecyl maltoside, about 34 mg to about 38 mg of DMA, and about 44 mg to about 66 mg of polyethylene glycol. An intranasal olanzapine composition may therefore comprise about 2.5% w/v to about 10% w/v of olanzapine (or a pharmaceutically acceptable salt thereof), about 0.20% w/v to about 0.50% w/v of dodecyl maltoside, about 34% w/v to about 38% w/v of DMA, and about 44% w/v to about 66% w/v of polyethylene glycol. In any embodiment, one or more doses of the intranasal olanzapine composition described above may be used to deliver a therapeutically effective amount of olanzapine to a subject in need thereof to treat a disorder, condition, or disease treatable with olanzapine, such as schizophrenia, schizoaffective disorder, bipolar disorder, and TRD.

In another example, each dose comprise may comprise about 2.5 mg to about 10 mg of olanzapine or a pharmaceutically acceptable salt thereof, about 0.25 mg to about 0.50 mg of dodecyl maltoside, about 34 mg to about 38 mg of DMA, and about 44 mg to about 66 mg of polyethylene glycol. An intranasal olanzapine composition may therefore comprise about 2.5% w/v to about 10% w/v of olanzapine (or a pharmaceutically acceptable salt thereof), about 0.20% w/v to about 0.50% w/v of dodecyl maltoside, about 34% w/v to about 38% w/v of DMA, and about 44% w/v to about 66% w/v of polyethylene glycol. In any embodiment, one or more doses of the intranasal olanzapine composition described above may be used to deliver a therapeutically effective amount of olanzapine to a subject in need thereof to treat a disorder, condition, or disease treatable with olanzapine, such as schizophrenia, schizoaffective disorder, bipolar disorder, and TRD.

In any embodiment, an intranasal olanzapine composition may comprise olanzapine or a pharmaceutically acceptable salt thereof that is at least substantially dissolved in the composition (herein "intranasal olanzapine solution"). As used herein, "substantially dissolved" indicates that at least 99.5% of the olanzapine is dissolved in the intranasal olanzapine composition. The intranasal olanzapine composition is therefore free of or substantially free of (i.e., comprising 0.5% w/v or less) of any solid particulate matter comprising olanzapine, including microparticles, microspheres, nanoparticles, and nanospheres. In any embodiment, at least 99.9% of the olanzapine may be dissolved in the intranasal olanzapine composition and comprise 0.1% w/v or less of any solid particulate matter comprising olanzapine. The intranasal olanzapine composition may be sprayable in liquid form and is not a dry powder formulation.

In any embodiment, an intranasal olanzapine composition may comprise a therapeutically effective amount of olanzapine or a pharmaceutically acceptable salt thereof that is at least substantially dissolved in the composition (herein "intranasal olanzapine solution"). As used herein, "substantially dissolved" indicates that at least 99.5% of the olanzapine is dissolved in the intranasal olanzapine composition. The intranasal olanzapine composition is therefore free of or substantially free of (i.e., comprising 0.5% w/v or less) of any solid particulate matter comprising olanzapine, including microparticles, microspheres, nanoparticles, and nanospheres. In any embodiment, at least 99.9% of the olanzapine may be dissolved in the intranasal olanzapine composition and comprise 0.1% w/v or less of any solid particulate matter comprising olanzapine. The intranasal olanzapine composition may be sprayable in liquid form and is not a dry powder formulation.

In any embodiment, an intranasal olanzapine solution may be at least substantially free of water (herein "non-aqueous intranasal olanzapine solution"). As used herein, "substantially free of water" indicates that the solution contains less than about 3%, less than about 2%, less than about 1%, less than about 0.5%, less than about 0.25%, or less than about 0.1% water.

In any embodiment, additional non-active excipients such as viscosity enhancers, texture modifiers, preservatives, stabilizers, and flavor or scent enhancing agents may be included in the intranasal olanzapine composition without affecting the efficacy of the olanzapine to provide a therapeutic benefit to the subject. An intranasal olanzapine solution may, in any embodiment, consist essentially of olanzapine, dodecyl maltoside, DMA, and polyethylene glycol, each in any amount disclosed at any point herein. Similarly, a non-aqueous intranasal olanzapine solution may, in any embodiment, consist essentially of olanzapine, dodecyl maltoside, DMA, and polyethylene glycol. Likewise, an intranasal olanzapine solution may, in any embodiment, consist of olanzapine, dodecyl maltoside, DMA, and polyethylene glycol. A non-aqueous intranasal olanzapine solution may, in any embodiment, consist of olanzapine, dodecyl maltoside, DMA, and polyethylene glycol, each in any amount disclosed at any point herein.

An intranasal olanzapine composition, which may be non-aqueous, a solution, or both, as disclosed herein, comprises about 0.1% w/v to about 1% w/v (i.e., 0.1 mg to 1 mg per 105 mg of composition) of dodecyl maltoside, such as dodecyl α- or β-D-maltoside. For example, in any embodiment, an intranasal olanzapine composition may comprise about 0.1% w/v to about 1% w/v of dodecyl maltoside, such as about 0.20% to about 0.50% of dodecyl maltoside (such as dodecyl-β-D-maltoside). Dodecyl maltoside is available commercially, such as that sold under the INTRAVAIL® tradename by Aegis Therapeutics, LLC. (San Diego, CA, USA), wholly owned subsidiary of Neurelis, Inc (San Diego, CA, USA).

An intranasal olanzapine composition, which may be non-aqueous, a solution, or both, as disclosed herein, comprises about 30% w/v to about 40% w/v of DMA, which includes about 30% w/v, about 31% w/v, about 32% w/v, about 33% w/v, about 34% w/v, about 35% w/v, about 36% w/v, about 37% w/v, about 38% w/v, about 39% w/v, about 40% w/v, and any value there between. A therapeutically effective dose of about 75 μL to about 150 μL of an intranasal olanzapine composition may comprise about 31 mg, about 32 mg, about 33 mg, about 34 mg, about 35 mg, about 36 mg, about 37 mg, about 38 mg, about 39 mg, or about 40 mg of DMA, or any value there between, such as about 37 mg to about 38 mg. DMA is available commercially, for example, from Belle Chemical Company (Metairie, LA, USA), Sigma Aldrich (St. Louis, MO, USA), and Eastman Chemicals (Kingsport, TN, USA).

An intranasal olanzapine composition, which may be non-aqueous, a solution, or both, as disclosed herein, additionally comprises about 40% w/v to about 70% w/v of polyethylene glycol having an average molecular weight of about 200 Da to about 1000 Da, preferably about 200 Da to about 700 Da, such as PEG-600, which has an average molecular weight of 600 Da. An intranasal olanzapine composition, which may be non-aqueous, a solution, or both, as disclosed herein, additionally comprises about 44% w/v to 66% w/v of polyethylene glycol having an average molecular weight of about 200 Da to about 1000 Da, preferably about 200 Da to about 700 Da, such as PEG-600, which has an average molecular weight of 600 Da. For example, an intranasal olanzapine composition may comprise about 44% w/v to about 60% w/v, about 50% w/v to about 60% w/v, about 55% w/v to about 66% w/v, about 52% w/v to about 62% w/v, or about 56% w/v to about 60% w/v of polyethylene glycol. A therapeutically effective dose of about 75 µL to about 150 µL of an intranasal olanzapine composition may comprise, for example, about 44 mg to about 66 mg of polyethylene glycol, such as about 52 mg to about 66 mg or about 54 mg to about 66 mg of polyethylene glycol.

In any embodiment, the polyethylene glycol may be a mixture of polyethylene glycol molecules differing in size and/or branching index that on average, produce a bulk average molecular weight of about 200 Da to about 1000 Da, such as about 200 Da to about 900 Da, about 200 Da to about 800 Da, about 200 Da to about 700 Da, about 300 Da to about 900 Da, about 300 Da to about 800 Da, about 300 Da to about 700 Da, about 400 Da to about 900 Da, about 400 Da to about 800 Da, about 400 Da to about 700 Da, about 500 Da to about 900 Da, about, about 500 Da to about 800 Da, about 500 Da to about 700 Da, or any value there between such as about 200 Da, about 300 Da, about 400 Da, about 500 Da, about 600 Da, about 700 Da, about 800 Da, about 900 Da, or about 1000 Da.

PEG-600 is available commercially, for example, from Dow Chemicals (Midland, MI, USA) under the CARBOWAX™ tradename, from BASF (Ludwigshafen, Germany) under the KOLLISOLV® tradename, from Sasol (Sandton, South Africa) under the NOVELUTION® tradename, from Double Bond Chemical (Taiwan) under the DOUBLEMER® tradename, and from Sigma Aldrich.

Advantageously, it has been observed that the intranasal olanzapine compositions, as described herein, do not support the growth of bacteria and therefore may be substantially free or free of any antibacterial agents or other preservatives. However, the use of an antibacterial does not preclude the therapeutic benefits of administering a therapeutically effective amount of olanzapine via an intranasal olanzapine composition, solution, or non-aqueous solution, as described herein. Therefore, any intranasal olanzapine composition (including non-aqueous solutions) as disclosed herein, may be free of or substantially free of any preservation, anti-degradation, antibacterial, or antifungal agent.

An intranasal olanzapine composition, as disclosed herein, may exhibit properties that are compatible with and do not irritate nasal mucosal membranes. Such properties include tonicity, osmolality, and viscosity. As such, the intranasal olanzapine compositions have been formulated to exhibit adequate drug solubility and stability and provide a vehicle for the delivery of the drug that is essentially non-irritating to the nasal mucosa.

A therapeutically effective dose of an intranasal olanzapine composition, as disclosed herein, may be administered to a subject in one or more volumes via the nasal mucosa of the subject. Such volumes include, for example, about 10 µL to about 200 µL, about 50 µL to about 150 µL, about 75 µL to about 125 µL, about 75 µL to about 100 µL, or about 125 µL. For example, a dose of about 1 mg to about 15 mg olanzapine (or a pharmaceutically acceptable salt thereof) may be administered in a volume of about 25 µL, about 50 µL, about 75 µL, about 100 µL, about 125 µL, or about 150 µL. A dose may be administered to a single nostril or split up between nostrils. For example, a dose of 2.5 mg olanzapine in about 100 µL, a dose of 5 mg olanzapine in about 100 µL, 7.5 mg olanzapine in 100 µL, 10 mg olanzapine in about 100 µL, or 15 mg olanzapine in about 100 µL may be administered in a single nostril. A dose of 5 mg may alternatively be administered as a dose of 2.5 mg olanzapine in about 100 µL in each nostril. Similarly, a dose of 10 mg olanzapine may alternatively be administered as a dose of 5 mg olanzapine in about 100 µL in each nostril. Likewise, a 15 mg olanzapine dose may be administered, for example, as 7.5 mg olanzapine in about 100 µL to each nostril. A therapeutically effective amount of olanzapine may be about 1 mg olanzapine to about 15 mg, such as about 2.5 mg to about 10 mg, about 2.5 mg to about 7.5 mg, about 2.5 mg to about 5 mg, about 5 mg to about 10 mg, about 5 mg to about 7.5 mg, about 7.5 mg to about 10 mg, about 1 mg to about 5 mg, about 1 mg to about 15 mg, about 2.5 mg to about 15 mg, about 5 mg to about 15 mg, about 2.5 mg, about 5 mg, about 7.5 mg, about 10 mg olanzapine, about 12 mg olanzapine, or about 15 mg olanzapine.

Methods of Use

Delivering olanzapine to a nasal mucosal membrane of a subject via any of the intranasal olanzapine compositions disclosed herein induces a rapid and effective therapeutic benefit to the subject. Further, intranasally administering an intranasal olanzapine composition, as disclosed herein, may achieve similar pharmacokinetic properties when compared to known formulations, such as those administered orally, intravenously, or intramuscularly. For example, one or more of the olanzapine $T_{max}$, $C_{max}$, and AUC achieved after administration of an intranasal olanzapine composition may be about 80% to about 125%, about 90% to about 125%, about 100% to about 125%, about 90% to about 110%, or about 80% to about 110% of the $T_{max}$, $C_{max}$, or AUC achieved, respectively, after intramuscular administration of olanzapine (e.g., ZYPREXA®). For example, the $C_{max}$ for 5 mg intramuscular (IM) olanzapine is reported to be about 4-5 times that of the oral dose (7 ng/mL) and $T_{max}$ for oral and IM olanzapine is reported to be about 15 to about 45 minutes. In comparison, 5 mg olanzapine administered via an intranasal olanzapine composition as disclosed herein may achieve a $C_{max}$ of about 22 ng/mL to about 44 ng/mL may be achieved within about 11 minutes to about 57 minutes ($T_{max}$). The $C_{max}$ for a 10 mg IM olanzapine is reported to be about 4 to about 5 times that of the 10 mg oral dose (14 ng/mL). In comparison, 10 mg of olanzapine administered via an intranasal olanzapine composition as described herein may achieve a $C_{max}$ of about 44.8 ng/mL to about 87.5 ng/mL within about 11 minutes to about 57 minutes ($T_{max}$). Bioavailability of olanzapine administered via an intranasal olanzapine composition as disclosed herein, may be comparable to olanzapine administered orally or intramuscularly, such as exhibiting an $AUC_{0-\infty}$ of about 123 ng·hr/ml to about 257 ng·hr/mL for a dose comprising 5 mg olanzapine or about 248 ng·hr/ml to about 356 ng·hr/mL for a dose comprising 10 mg olanzapine.

A therapeutically effective amount of olanzapine may be administered to a nasal mucosa of a subject in need thereof via one or more doses of an intranasal olanzapine composition. In some embodiments, the intranasal olanzapine composition which may be non-aqueous, a solution, or both, comprises about 1% w/v to about 15% w/v of olanzapine, about 0.1% w/v to about 1% w/v of dodecyl maltoside, about 30% w/v to about 40% w/v of DMA, and about 40% w/v to about 70% w/v of polyethylene glycol. In some embodiments, the ratio of the polyethylene glycol to the N, N-dimethylacetamide is from about 4:1 to about 1:4. In some embodiments, the ratio of the polyethylene glycol to the N,N-dimethylacetamide is about 3:2. Each dose administered may comprise a therapeutically effective amount of olanzapine (or a pharmaceutically acceptable salt thereof). In other embodiments, each dose administered may comprise about 1 mg to about 10 mg, or about 2.5 mg to about 15 mg, or about 2.5 mg to about 10 mg of olanzapine (or a pharmaceutically acceptable salt thereof). Olanzapine may be administered via an intranasal olanzapine composition as disclosed herein to treat any condition, disorder, or disease treatable with olanzapine. Several example conditions will be described now, merely to provide examples of conditions that can be treated with olanzapine via an intranasal olanzapine composition disclosed herein, but not to limit the wide variety of conditions which may be treatable in this way.

In some embodiments, Olanzapine administered via an intranasal olanzapine composition as disclosed herein may result in a lower incidence of adverse events, less serious adverse events, or a combination thereof compared with olanzapine administered via intramuscular injection or intravenous injection.

Acute Agitation

For example, olanzapine may be administered via an intranasal olanzapine composition, as disclosed herein, to treat acute agitation associated with schizophrenia, schizoaffective disorder, and bipolar disorder. Such an intranasal olanzapine composition may be used as a monotherapy or a co-therapy with one or more additional agents commonly used in the treatment of acute agitation in these conditions, such as, but not limited to, lithium and valproate. The methods described herein are suitable for treating a subject in any stage of the condition/disorder. Administration may be carried out at any time before or after the onset of the acute agitation.

A method of treating acute agitation associated with schizophrenia, schizoaffective disorder, or bipolar disorder in a subject in need thereof may comprise administering a therapeutically effective amount of olanzapine via an intranasal olanzapine composition to at least one nasal mucosal membrane in at least one nostril of the subject. A therapeutically effective amount of olanzapine for an adult subject may be between about 1 and about 15 mg, for example, 2.5 mg, 5 mg, 7.5 mg, 10 mg, 12 mg, or 15 mg of olanzapine or a pharmaceutically acceptable salt thereof. In some embodiments, treating acute agitation associated with schizophrenia, schizoaffective disorder, or bipolar disorder in a subject in need thereof comprises a change from baseline in the Positive and Negative Syndrome Scale (PANSS) Excited Component ((i.e., poor impulse control, tension, hostility, uncooperativeness and excitement items) with at least 1 individual item score ≥4 using a 1-7 scoring system (1=absent, 4=moderate, 7=extreme)) at about 2 hours post administration. In some embodiments, treating acute agitation associated with schizophrenia, schizoaffective disorder, or bipolar disorder in a subject in need thereof comprises an improvement from baseline in the Positive and Negative Syndrome Scale (PANSS) Excited Component at about 2 hours post administration.

As such, in another aspect, the present disclosure provides a method of treating acute agitation associated with schizophrenia, schizoaffective disorder, or bipolar disorder in a subject in need thereof comprising: intranasally administering a first volume of an intranasal olanzapine composition, which may be non-aqueous, a solution, or both, comprising about 1 mg to about 15 mg of olanzapine (or a pharmaceutically acceptable salt thereof), about 0.20% w/v to about 0.50% w/v of dodecyl maltoside, about 30% w/v to about 40% w/v of DMA, and about 40% w/v to about 70% w/v of polyethylene glycol to a nasal mucosal membrane of the subject. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. The therapeutically effective amount of olanzapine may be administered via one or more doses of the intranasal olanzapine composition.

Administering a therapeutically effective amount of olanzapine via the intranasal olanzapine composition may comprise spraying one or more volumes of the intranasal olanzapine composition into each nostril, such as spraying a first volume of the intranasal olanzapine composition into the first nostril then spraying a second volume of the intranasal olanzapine composition into a second nostril. Optionally, a third volume and/or fourth volume of the intranasal olanzapine composition may be administered after the first and second volumes shortly thereafter. In any embodiment, one or more volumes may be administered to achieve administration of a therapeutically effective dose of olanzapine.

If the acute agitation of the subject is not satisfactorily treated within about 2 hours to about 4 hours of a first administration, the intranasal olanzapine composition may be administered a second time, and if again, not satisfactorily treated within about 2 hours to about 4 hours, administered a third time. As such, in another aspect, the present disclosure provides a method of treating acute agitation associated with schizophrenia, schizoaffective disorder, or bipolar disorder comprising: administering a first volume of an intranasal olanzapine composition disclosed herein, to a nasal mucosal membrane of the subject during or before acute agitation, wherein when adequate cessation or prevention of the agitation is not achieved within about 2 hours, about 3 hours, or about 4 hours after the administering of the first volume, one or more subsequent volumes of the intranasal olanzapine composition are administered to the subject. In some embodiments, the intranasal olanzapine composition comprises a therapeutically effective amount of olanzapine or a pharmaceutically acceptable salt thereof. In some embodiments, the therapeutically effective amount of olanzapine or a pharmaceutically acceptable salt thereof is about 1 mg to about 15 mg of olanzapine (or a pharmaceutically acceptable salt thereof). In some embodiments, the intranasal olanzapine composition further comprises about 0.20 mg to about 0.50 mg of dodecyl maltoside, about 30% w/v to about 40% w/v of DMA, and about 40% w/v to about 70% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. For example, an intranasal olanzapine composition, which may be non-aqueous, a solution, or both, comprising about 2.5 mg to about 15 mg of olanzapine (or a pharmaceutically acceptable salt thereof), about 0.20 mg to about 0.50 mg of dodecyl maltoside, about 34% w/v to about 38% w/v of DMA, and about 44% w/v to about 66% w/v of polyethylene glycol may be administered in a first volume and upon inadequate cessation of the acute agitation, a second volume of the intranasal olanzapine composition may be administered. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. The second volume may be identical in volume and strength as the first dose or may be different. Optionally, if adequate cessation of the acute agitation, is not achieved within about 2 hours, about 3 hours, or about 4 hours, the method may further comprise administering a third volume of the intranasal olanzapine composition.

Depressive Episodes Associated with Bipolar I Disorder

Olanzapine may be administered via an intranasal olanzapine composition, as disclosed herein, to treat depressive episodes associated with bipolar I disorder in adults, children, or adolescents (e.g., ages 10-17). In any embodiment, an intranasal olanzapine composition may be used as either as a monotherapy or a co-therapy with one or more additional agents commonly used to treat depression associated with bipolar disorder, such as fluoxetine. Administering a therapeutically effective amount of olanzapine via an intranasal olanzapine composition disclosed herein to a subject in need thereof may reduce the severity or incidence of depressive episodes associated with bipolar I disorder. In one example, acute bipolar depression may be treated by administering a therapeutically effective amount of olanzapine via the intranasal olanzapine composition disclosed herein at any time before or after onset of the acute bipolar depression. For example, in any embodiment, a subject diagnosed with bipolar I disorder may be treated with a therapeutically effective dose at least once daily as part of a maintenance regimen. In some embodiments, treating depressive episodes associated with bipolar I disorder in adults, children, or adolescents (e.g., ages 10-17) comprises a change from baseline in the adult, child or adolescent's Montgomery-Asberg Depression Rating Scale (MADRS), a 10-item clinician-rated scale with total scores ranging from 0 to 60. In some embodiments, treating depressive episodes associated with bipolar I disorder in adults, children, or adolescents (e.g., ages 10-17) comprises an improvement in the adult, child or adolescent's MADRS score after administration for about 8 weeks.

A method of treating acute bipolar depression in a subject in need thereof may comprise administering a therapeutically effective amount of olanzapine via an intranasal olanzapine composition disclosed herein to at least one nasal mucosal membrane in at least one nostril. A therapeutically effective amount of olanzapine for an adult subject may be, for example, between about 1 mg and about 15 mg of olanzapine (or a pharmaceutically acceptable salt thereof) once daily, which may be administered according to the above disclosure to treat depressive episodes associated with bipolar I disorder, optionally in combination with fluoxetine, such as about 20 mg of fluoxetine, which may be administered at substantially the same time by any administration route. A therapeutically effective amount of olanzapine for an adult subject may be, for example, about 5 mg of olanzapine (or a pharmaceutically acceptable salt thereof) once daily, which may be administered according to the above disclosure to treat depressive episodes associated with bipolar I disorder, optionally in combination with fluoxetine, such as about 20 mg of fluoxetine, which may be administered at substantially the same time by any administration route. For example, fluoxetine may be administered via an oral dosage form. A therapeutically effective amount of olanzapine in a child or adolescent subject may be, for example, about 2.5 mg of olanzapine (or a pharmaceutically acceptable salt thereof) once daily, which may be administered according to the above disclosure to treat depressive episodes associated with bipolar I disorder, optionally in combination with fluoxetine, such as about 20 mg of fluoxetine, which may be administered at substantially the same time by any administration route. For example, fluoxetine may be administered via an oral dosage form.

As such, in another aspect, the present disclosure provides a method of treating depressive episodes associated with bipolar I disorder in a subject in need thereof comprising: intranasally administering a first volume of an intranasal olanzapine composition, which may be non-aqueous, a solution, or both, comprising about 1 mg to about 15 mg of olanzapine (or a pharmaceutically acceptable salt thereof), about 0.20% w/v to about 0.50% w/v of dodecyl maltoside, about 30% w/v to about 40% w/v of DMA, and about 40% w/v to about 70% w/v of polyethylene glycol to a nasal mucosal membrane of the subject. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. The therapeutically effective amount of olanzapine may be administered via one or more doses of the intranasal olanzapine composition.

Administering a therapeutically effective amount of olanzapine via the intranasal olanzapine composition may comprise spraying one or more volumes of the intranasal olanzapine composition disclosed herein into each nostril, such as spraying a first volume of the intranasal olanzapine composition disclosed herein into the first nostril then spraying a second volume of the intranasal olanzapine composition into a second nostril. Optionally, a third volume and/or fourth volume of the intranasal olanzapine composition disclosed herein may be administered after the first and second volumes. In any embodiment, one or more doses may be administered to achieve administration of a therapeutically effective amount of olanzapine.

Bipolar I Disorder (Manic or Mixed Episodes)

Olanzapine may be administered via an intranasal olanzapine composition as disclosed herein to treat a manic and/or mixed episodes associated with bipolar I disorder in adult and adolescents (e.g., ages 13-17). In any embodiment, administration of olanzapine via an intranasal olanzapine composition disclosed herein may be utilized as either as a monotherapy or a co-therapy with one or more additional agents commonly used to treat mania and mixed episodes associated with bipolar disorder, such as lithium or sodium valproate.

Administering a therapeutically effective amount of olanzapine via such an intranasal olanzapine composition disclosed herein to a subject in need thereof may reduce severity, frequency, or length of one acute bipolar manic episode/s and/or a mixed episode/s in a subject experiencing such symptoms. In one example, manic and/or mixed episodes associated with bipolar I disorder may be treated by administering a therapeutically effective amount of olanzapine via the intranasal olanzapine composition disclosed herein at any time before or after onset of the manic episode and/or a mixed episode. For example, a subject diagnosed with bipolar I disorder may be treated once daily as a maintenance treatment. In some embodiments, Administering a therapeutically effective amount of olanzapine via such an intranasal olanzapine composition disclosed herein to a subject in need thereof may result in a change from baseline in the subjects Young Mania Rating Scale (Y-MRS), an 11-item clinician-rated scale traditionally used to assess the degree of manic symptomatology (irritability, disruptive/ aggressive behavior, sleep, elevated mood, speech, increased activity, sexual interest, language/thought disorder, thought content, appearance, and insight) in a range from 0 (no manic features) to 60 (maximum score). In some embodiments, administering a therapeutically effective amount of olanzapine via such an intranasal olanzapine composition disclosed herein to a subject in need thereof may result in an improvement in the subjects Y-MRS score.

A method of treating manic and/or mixed episodes associated with bipolar I disorder in a subject in need thereof may comprise administering a therapeutically effective amount of olanzapine via one or more doses of the intranasal olanzapine composition disclosed herein to a nasal mucosal membrane of the subject. A therapeutically effective amount of olanzapine for treating manic and/or mixed episodes associated with bipolar I disorder in a child or adolescent subject may be, for example, from about 1 mg to about 15 mg of olanzapine (or a pharmaceutically acceptable salt thereof). A therapeutically effective amount of olanzapine for treating manic and/or mixed episodes associated with bipolar I disorder in a child or adolescent subject may be, for example, about 2.5 mg to about 5 mg of olanzapine (or a pharmaceutically acceptable salt thereof) once daily, increasing to a target maintenance dosage of 10 mg/day. A therapeutically effective amount of olanzapine may be administered via an intranasal olanzapine composition disclosed herein to treat manic and/or mixed episodes associated with bipolar I disorder, optionally in combination with fluoxetine, such as about 20 mg of fluoxetine, which may be administered at substantially the same time by any administration route. For example, fluoxetine may be administered via an oral dosage form.

A therapeutically effective amount of olanzapine for treating manic and/or mixed episodes associated with bipolar I disorder in an adult subject may be, for example, about 10 mg of olanzapine (or a pharmaceutically acceptable salt thereof) once daily, which may be administered according to the above disclosure to treat for treating manic and/or mixed episodes associated with bipolar I disorder, optionally in combination with a therapeutic amount of lithium (e.g., 50 µg/mL to 125 µg/mL), which may be administered at substantially the same time by any administration route.

As such, in another aspect, the present disclosure provides a method of treating manic and/or mixed episodes associated with bipolar I disorder in a subject in need thereof comprising: intranasally administering a first volume of an intranasal olanzapine composition described herein to a nasal mucosal membrane of the subject. In some embodiments, the intranasal olanzapine composition may be non-aqueous, a solution, or both. In some embodiments, the therapeutically effective amount of olanzapine or a pharmaceutically acceptable salt thereof is about 1 mg to about 15 mg of olanzapine (or a pharmaceutically acceptable salt thereof). In some embodiments, the intranasal olanzapine composition further comprises about 0.20% w/v to about 0.50% w/v of dodecyl maltoside, about 30% w/v to about 40% w/v of DMA, and about 40% w/v to about 70% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2.

Administering a therapeutically effective amount of olanzapine via the intranasal olanzapine composition disclosed herein may comprise spraying one or more volumes of the intranasal olanzapine composition into each nostril, such as spraying a first volume of the intranasal olanzapine composition into the first nostril then spraying a second volume of the intranasal olanzapine composition into a second nostril. Optionally, a third volume and/or fourth volume of the intranasal olanzapine composition may be administered after the first and second volumes. In any embodiment, one or more doses may be administered to achieve administration of a therapeutically effective amount of olanzapine.

Schizophrenia and Related Disorders

Olanzapine, intranasally administered via an intranasal olanzapine composition described herein, as disclosed herein, may also be used as a maintenance therapy to treat schizophrenia and related psychotic disorders, such as schizoaffective disorder in adults and in adolescent (e.g., ages 13-17) subjects. Such an intranasal olanzapine composition as described herein may be used as a monotherapy or a co-therapy with one or more additional agents commonly used to treat schizophrenia or schizoaffective disorder, such as amisulpride.

A method of treating or managing schizophrenia or a related psychotic disorder in a subject in need thereof may comprise applying a therapeutically effective amount of olanzapine via one or more doses of the intranasal olanzapine composition as described herein to a nasal mucosal membrane of the subject. For example, intranasally administering a therapeutically effective amount of olanzapine via the intranasal olanzapine composition described herein may comprise spraying one or more doses of the intranasal olanzapine composition into each nostril, such as spraying a first dose of the intranasal olanzapine composition into the first nostril then spraying a second dose of the intranasal olanzapine composition into a second nostril. Optionally, a third dose and/or fourth dose of the intranasal olanzapine composition may be administered after the first and second doses. In any embodiment, one or more doses may be administered to achieve administration of a therapeutically effective amount of olanzapine.

As a maintenance therapy, olanzapine intranasally administered to a subject via an intranasal olanzapine composition as disclosed herein may be used in preventing (i.e., inhibiting the onset of) or managing (e.g., reducing the incidence of, severity of, or length of) one or more positive symptoms of schizophrenia or schizoaffective disorder such as, but not limited to, delusions, hallucinations, disorganized thinking or speech, trouble concentrating, and movement disorders. Olanzapine intranasally administered to a subject via an intranasal olanzapine composition as disclosed herein may be used in preventing (i.e., inhibiting the onset of) or managing (e.g., reducing the incidence of, severity of, or length of) one or more negative symptoms of schizophrenia or schizoaffective disorder such as, but not limited to, lack of pleasure, trouble with speech, flattening, withdrawal, struggling with basic daily life, and lack of follow-through.

In some embodiments, olanzapine, intranasally administered via an intranasal olanzapine composition described herein, as disclosed herein, may also be used as a maintenance therapy to treat schizophrenia and related psychotic disorders, such as schizoaffective disorder in adults and in adolescent (e.g., ages 13-17) subjects results in an improvement in the subject's Brief Psychiatric Rating Scale (BPRS), an improvement in the subject's Clinical Global Impression (CGI) score, an improvement in the subject's Positive and Negative Symptoms Scale (PANSS) score, an improvement in the subject's e Scale for Assessing Negative Symptoms (SANS) score. The BPRS, a multi-item inventory of general psychopathology is traditionally used to evaluate the effects of drug treatment in schizophrenia. The BPRS psychosis cluster (conceptual disorganization, hallucinatory behavior, suspiciousness, and unusual thought content) is considered a particularly useful subset for assessing actively psychotic schizophrenic patients. A second traditional assessment, the CGI, reflects the impression of a skilled observer, fully familiar with the manifestations of schizophrenia, about the overall clinical state of the patient.

Therefore, the present disclosure provides a method of treating a subject diagnosed with one or more of schizophrenia or schizoaffective disorder comprising administering a therapeutically effective amount of olanzapine via one or more doses of an intranasal olanzapine composition described herein to a nasal mucosal membrane of the subject. In some embodiments, the intranasal olanzapine composition may be non-aqueous, a solution, or both. In some embodiments, the therapeutically effective amount of olanzapine or a pharmaceutically acceptable salt thereof is about 1 mg to about 15 mg of olanzapine (or a pharmaceutically acceptable salt thereof). In some embodiments, the intranasal olanzapine composition further comprises about 0.20% w/v to about 0.50% w/v of dodecyl maltoside, about 30% w/v to about 40% w/v of DMA, and about 40% w/v to about 70% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. Schizophrenia and/or schizoaffective disorder may be treated by administering a therapeutically effective amount of olanzapine via the intranasal olanzapine composition at least once a day, such as once a day, twice a day, or three times a day. In any embodiment, an adult subject may be administered a first dose on a first day, such as about 5 mg olanzapine, and on one or more subsequent days be administered a higher olanzapine dose, such as 7.5 mg olanzapine or 10 mg olanzapine, with a target maintenance dose of 10 mg/day.

Administering a therapeutically effective amount of olanzapine via the intranasal olanzapine composition disclosed herein may comprise spraying one or more volumes of the intranasal olanzapine composition into each nostril, such as spraying a first volume of the intranasal olanzapine composition into the first nostril then spraying a second volume of the intranasal olanzapine composition into a second nostril. Optionally, a third volume and/or fourth volume of the intranasal olanzapine composition may be administered after the first and second volumes. In any embodiment, one or more doses may be administered to achieve administration of a therapeutically effective amount of olanzapine.

Treatment-Resistant Depression (TRD)

Olanzapine, intranasally administered via an intranasal olanzapine composition described herein may also be used to treat TRD in adult subjects. Such an intranasal olanzapine composition may be used as a monotherapy or a co-therapy with one or more additional agents commonly used to treat depression, such as fluoxetine.

A method of treating or managing TRD in a subject in need thereof may comprise applying a therapeutically effective amount of olanzapine via one or more doses of the intranasal olanzapine composition described herein to a nasal mucosal membrane of the subject. In some embodiments, the therapeutically effective amount of olanzapine or a pharmaceutically acceptable salt thereof is about 1 mg to about 15 mg of olanzapine (or a pharmaceutically acceptable salt thereof). In some embodiments, the intranasal olanzapine composition further comprises about 0.20% w/v to about 0.50% w/v of dodecyl maltoside, about 30% w/v to about 40% w/v of DMA, and about 40% w/v to about 70% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. A therapeutically effective amount of olanzapine may be about 5 mg olanzapine, 7.5 mg olanzapine, or 10 mg olanzapine (or an equivalent amount of a salt thereof).

As such, in another aspect, the present disclosure provides a method of treating TRD in a subject in need thereof comprising administering a therapeutically effective amount of olanzapine via one or more doses of an intranasal olanzapine composition described herein, which may be non-aqueous, a solution, or both disclosed herein, the intranasal olanzapine composition comprising about 1% w/v to about 15% w/v olanzapine (or a pharmaceutically acceptable salt thereof), about 0.1% w/v to about 1% w/v of dodecyl maltoside, about 30% w/v to about 40% w/v DMA, and about 40% w/v to about 70% w/v of polyethylene glycol. For example, a therapeutically effective dose of about 75 μL to about 150 μL of the intranasal olanzapine composition may comprise about 2.5 mg to about 15 mg of olanzapine (or a pharmaceutically acceptable salt thereof), about 0.20% w/v to about 0.50% w/v of dodecyl maltoside, about 34% w/v to about 38% w/v of DMA, and about 44% w/v to about 66% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2.

In some embodiments, administering a therapeutically effective amount of olanzapine via one or more doses of an intranasal olanzapine composition described herein results in a reduction in the subject's total MADRS compared to baseline. In some embodiments, treating or managing TRD in a subject in need thereof may comprise applying a therapeutically effective amount of olanzapine via a single daily dose of the intranasal olanzapine composition described herein to a nasal mucosal membrane of the subject.

TRD may be treated by administering a therapeutically effective amount of olanzapine via the intranasal olanzapine composition at least once a day, such as once a day, twice a day, or three times a day. In any embodiment, an adult subject may be administered a first dose on a first day, such as about 5 mg olanzapine, and on one or more subsequent days be administered a higher olanzapine dose, such as 7.5 mg olanzapine or 10 mg olanzapine, with a target maintenance dose of 10 mg/day. Administering a therapeutically effective amount of olanzapine via the intranasal olanzapine composition may comprise spraying one or more volumes of the intranasal olanzapine composition into each nostril, such as spraying a first volume of the intranasal olanzapine composition into the first nostril then spraying a second volume of the intranasal olanzapine composition into a second nostril. Optionally, a third volume and/or fourth volume of the intranasal olanzapine composition may be administered after the first and second volumes. In any embodiment, one or more doses may be administered to achieve administration of a therapeutically effective amount of olanzapine.

Other Methods of Use

The intranasal olanzapine compositions, as disclosed herein, may also be used to treat one or more of depression, agitation associated with neurodevelopment disorders such as autism spectrum disorder, rage attacks associated with obsessive compulsive disorders (OCDs), Tourette's syndrome, and/or autism spectrum disorder, and the like. Therefore, the present disclosure provides a method of inhibiting, or reducing one or more of the incidence, severity, or length of one of these conditions or symptoms in a subject in need thereof (e.g., diagnosed with OCD, Tourette's syndrome, autism spectrum disorder) comprising administering a therapeutically effective amount of olanzapine via one or more doses of an intranasal olanzapine composition disclosed herein, the intranasal olanzapine composition, described herein to a nasal mucosal membrane of the subject. In some embodiments, the intranasal olanzapine composition may be non-aqueous, a solution, or both. In some embodiments, the therapeutically effective amount of olanzapine or a pharmaceutically acceptable salt thereof is about 1 mg to about 15 mg of olanzapine (or a pharmaceutically acceptable salt thereof). In some embodiments, the intranasal olanzapine composition further comprises about 0.20% w/v to about 0.50% w/v of dodecyl maltoside, about 30% w/v to about 40% w/v of DMA, and about 40% w/v to about 70% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. For example, a therapeutically effective dose of about 75 μL to about 150 μL of the intranasal olanzapine composition, as disclosed herein, may comprise about 2.5 mg to about 10 mg of olanzapine (or a pharmaceutically acceptable salt thereof), about 0.20 mg to about 0.50 mg of dodecyl maltoside, about 34% w/v to about 38% w/v of DMA, and about 44% w/v to about 66% w/v of polyethylene glycol. In another example, a dose of the intranasal olanzapine composition may comprise about 2.5 mg to about 15 mg of olanzapine (or a pharmaceutically acceptable salt thereof), about 0.20% w/v to about 0.50% w/v of dodecyl maltoside, about 30% w/v to about 40% w/v of DMA, and about 40% w/v to about 70% w/v of polyethylene glycol. In another example, a therapeutically effective dose of about 75 μL to about 150 μL of the intranasal olanzapine composition may comprise about 2.5 mg to about 10 mg of olanzapine (or a pharmaceutically acceptable salt thereof), about 0.20% w/v to about 0.50% w/v of dodecyl maltoside, about 34% w/v to about 38% w/v of DMA, and about 44% w/v to about 66% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2.

Therapeutic Effect

Intranasally administering a therapeutically effective amount of olanzapine via the intranasal olanzapine composition as described herein to a subject in need thereof may be effective at reducing one or more quantitatively measurable symptoms of schizophrenia, schizoaffective disorder, bipolar I disorder, and/or TRD. In any embodiment, a therapeutically effective amount of the intranasal olanzapine composition may comprise: about 1 mg to about 15 mg olanzapine; about 0.1 mg to about 1 mg of dodecyl maltoside; about 30% w/v to about 40% w/v DMA, and about 40% w/v to about 70% w/v of polyethylene glycol and is optionally non-aqueous, a solution, or both. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. Intranasal administration of such a composition, comprising a therapeutically effective amount of olanzapine, may provide one or more therapeutic benefits to the subject, some of which may be quantitatively or semi-quantitatively measured according to the various assessments described herein below.

For example, in any embodiment, intranasally administering a therapeutically effective amount of olanzapine via an intranasal olanzapine composition, as disclosed herein, to a subject may reduce a positive score, a negative score, or a total (combined) PANSS (Positive and Negative Syndrome Scale) score of the subject. PANSS is a medical sale used for measuring symptom severity of patients with schizophrenia and is outlined in Table 1 below. A score of 1 is given as the lowest score for each item and as such, a patient will receive a minimum total score of 30.

TABLE 1

| Positive Scale (min. score = 7, max. score = 49) | Negative Scale (min. score = 7, max. score = 49) | General Psychopathology Scale (min. score = 16; max. score = 112) |
|---|---|---|
| Delusions | Blunted Affect | Somatic Concern |
| Conceptual Disorganization | Emotional Withdrawal | Anxiety |
| Hallucinations | Poor Rapport | Guilt Feelings |
| Excitement | Passive/Apathetic Social Withdrawal | Tension |
| Grandiosity | Difficulty in Abstract Thinking | Mannerisms and Posturing |
| Suspiciousness/ persecution | Lack of Spontaneity and Flow of Conversation | Depression |
| Hostility | Stereotyped Thinking | Uncooperativeness |
|  |  | Motor Retardation |
|  |  | Unusual Thought Content |
|  |  | Disorientation |
|  |  | Poor Attention |
|  |  | Lack of judgement and Insight |
|  |  | Disturbance of Volition |
|  |  | Poor Impulse Control |
|  |  | Preoccupation |
|  |  | Active Social Avoidance |

In another example, in any embodiment, intranasally administering a therapeutically effective amount of olanzapine via an intranasal olanzapine composition to a subject with schizophrenia may reduce a score of the subject on the Clinical Global Impression-Schizophrenia (CGI-S) scale. The CGI-S scale is a rating scale of symptom severity, treatment response, and the efficacy of treatment studies of patients with mental disorders comprising a three-item observer-rated scale assessing Severity of illness, Global improvement, and Efficacy Index. The Severity scale is a 7-point scale that ranks a patient from 1 (normal, not ill at all) to 7 (amongst the most extremely ill patients). The Improvement scale ranks a patient from 1 (very much improved) to 7 (very much worse). The Efficacy Index is a 4×4 rating scale that assesses the therapeutic effect and associated side effects from marked/vast improvement to unchanged/worse with side effects ranging from none to outweigh the therapeutic effect.

In yet another example and in any embodiment, intranasally administering a therapeutically effective amount of olanzapine via an intranasal olanzapine composition, as disclosed herein, to a subject experiencing agitation may improve the subject's score on the Agitation Calmness Evaluation Scale (ACES) and/or Agitated Behavior Scale (ABS). ACES consists of a single item that rates overall agitation and sedation at the time of evaluation, and ranges from 1 (marked agitation) to 9 (unarousable), where 7 represents marked calmness. ABS measures behavioral aspects of agitation and is calculated on a point scale out of 56, summing the response values for each of 14 questions, each describing a form of agitated behavior. Values for each question range from 1 (absent) to 4 (present-extreme).

In yet another example and in any embodiment, intranasally administering a therapeutically effective amount of olanzapine via an intranasal olanzapine composition, as disclosed herein, to a subject may reduce a total score on the Brief Psychiatric Rating Scale (BPRS). BPRS scores a variety of symptoms, such as somatic concerns, anxiety, emotional withdrawal, conceptual disorganization, feelings of guilt, tension, mannerisms/posturing, grandiosity, depressive mood, hostility, suspiciousness, hallucinatory behavior, motor retardation, uncooperativeness, unusual thoughts, blunted affect, excitement, and disorientation on a scale of 1 (not present) to 7 (extremely severe).

In another example and in any embodiment, intranasally administering a therapeutically effective amount of olanzapine via an intranasal olanzapine composition, as disclosed herein, to a subject experiencing episodes of bipolar depression to reduce a score of the subject on the Hamilton Depression Rating Scale. The Hamilton Depression (HAM-D) is a multiple-item questionnaire assessing various symptoms such as depressed mood, feelings of guilt, suicidal thoughts, insomnia, work/interest, retardation, agitation, anxiety, GI symptoms, somatic symptoms, genital symptoms, hypochondriasis, weight loss, and insight. Each item is scored on a 3-point or 5-point scale with 0 being normal or not present and higher numbers representing increased severity of the symptom.

In another example and in any embodiment, intranasally administering a therapeutically effective amount of olanzapine via an intranasal olanzapine composition to a subject, as disclosed herein, experiencing episodes of bipolar depression may improve a score of the subject on one or more of the Loss of Motivated Behavior HAM-D factor, HAM-D Suicide Item, Hamilton Anxiety Scale, and Beck's Depression Inventory. Each of these tests are familiar to one of ordinary skill in the art.

In another example and in any embodiment, intranasally administering a therapeutically effective amount of olanzapine via an intranasal olanzapine composition, as disclosed herein, to a subject experiencing episodes of bipolar depression may improve a subject's Young Mania Rating Scale (YMRS) score. YMRS has 11 items and based on the subject's subjective report of their own clinical condition over the previous 48 hours.

Methods of Manufacture

In any embodiment, an intranasal olanzapine composition may be substantially free of olanzapine microparticles, nanoparticles, or combinations thereof. The order of addition of any of the components of the intranasal olanzapine composition is not particularly critical, provided the olanzapine is fully or at least substantially dissolved in the composition. For example, in any embodiment, an intranasal olanzapine composition, which may be non-aqueous, a solution, or both, as disclosed herein, may be made by dissolving the alkyl glycoside (e.g., dodecyl maltoside) into DMA after which olanzapine may be added and dissolved. Polyethylene glycol may then be added and the resulting mixture may be stirred.

The formulation process may be adjusted to take variations in the intranasal olanzapine composition into consideration. For example, an intranasal olanzapine composition may be prepared by first combining DMA and olanzapine and mixing until the ingredients are homogenous, adding dodecyl maltoside, and mixing until the dodecyl maltoside is dissolved and the solution is homogenous. The mixture may be brought to volume by adding a sufficient amount of polyethylene glycol to achieve the final target weight of the intranasal olanzapine composition. Intranasal olanzapine composition manufactured according to this process may be prepared in different doses of olanzapine, such as, but not limited to 2.5 mg, 5.0 mg, 7.5 mg, 10 mg, 12 mg, or 15 mg. Being suitable for administration to the nasal mucosal membrane, an intranasal olanzapine composition, as disclosed herein, may be formulated as a sprayable olanzapine composition comprising 1 mg to about 15 mg of olanzapine (or a pharmaceutically acceptable salt thereof) in a intranasally-administrable volume, such as about 25 µL, 50 µL to about 500 µL, about 100 µL to about 250 µL, about 75 µL to about 125 µL, about 75 µL, about 100 µL, or about 125 µL.

Therefore, in another aspect, the present disclosure provides a device adapted for intranasal delivery of any intranasal olanzapine composition disclosed herein. Such a device may be provided or supplied as a pre-primed device or may be primed by the subject before use. A device may be a metered device and/or a single-dose device, a bi-dose device, or a multi-dose device. Such devices typically comprise a piston, a swirl chamber, an actuator and deliver a spray formed when a composition in the reservoir is forced out through the swirl chamber. Devices may be actuated by a subject by holding the device between a second and third finger with a thumb on the actuator. A device may additionally include a pressure point mechanism to ensure reproducibility of the actuation force and emitted plume/spray characteristics.

Administration Devices

Another aspect of the present disclosure is directed to a device adapted for nasal delivery of a composition as described above to a subject, the device comprising a reservoir configured to contain any of the intranasal olanzapine compositions as described above. In particular, such a composition may comprise about 1% w/v to about 15% w/v olanzapine, about 0.1% w/v to about 1% w/v of dodecyl maltoside, about 30% w/v to about 40% w/v DMA, and about 40% w/v to about 70% w/v of polyethylene glycol. For example, a composition may comprise about 2.5% w/v to about 12% w/v olanzapine, about 0.20% w/v to about 0.50% w/v, about 30% w/v to about 40% w/v of DMA, and about 44% w/v to about 66% w/v of polyethylene glycol. In some embodiments, the ratio of the polyethylene glycol to the N,N-dimethylacetamide is from about 4:1 to about 1:4. In some embodiments, the ratio of the polyethylene glycol to the N,N-dimethylacetamide is about 3:2. Such a device may be optionally supplied as a pre-primed device. Such a device may optionally be a multi-dose device having a single or multiple reservoirs; in the latter case, each containing a single dose of drug an intranasal olanzapine composition. Each single dose reservoir may comprise, for example, 25 µL to about 200 µL of the intranasal olanzapine composition. Each multiple dose reservoir may contain up to 20 mL or more of the intranasal olanzapine composition, dependent on its therapeutic use.

The term "pre-primed," as used herein, refers to a device, such as a nasal spray which can deliver a pharmaceutical composition to a patient in need thereof with the first actuation of the spray pump, i.e., without the need to prime the pump prior to dosing, such as by actuating the pump one or more times until a spray appears. The term "actuation," as used herein, refers to operation of the device such that the pharmaceutical composition is delivered therefrom.

Pre-primed single- and multi-dose devices consisting of a reservoir, a piston, and a swirl chamber are suitable devices for delivering an intranasal olanzapine composition as described herein. The spray is formed when the liquid is forced out through the swirl chamber. These devices are held between the second and the third fingers with the thumb on the actuator. A pressure point mechanism incorporated in some devices secures reproducibility of the actuation force and emitted plume characteristics. Currently, marketed nasal migraine drugs like IMITREX® (GlaxoSmithKline, Brentford, UK) and ZOMIG® (Pfeiffer/Aptar single-dose device), the marketed influenza vaccine Flu-Mist (Becton Dickinson single-dose spray device), and the intranasal formulation of naloxone for opioid overdose rescue, NARCAN NASAL® (narcan.com; Adapt Pharma) are delivered with this type of device.

For drugs intended for single administration or sporadic use and where tight control of the dose and composition is of importance, single-dose or bi-dose spray devices are preferred, such as those available from Aptar (Crystal Lake, IL, USA). Other suitable devices that can be employed to deliver the compositions described herein include, without limitation, a simple variant of a single-dose spray device (MAD™) that is offered by LMA (LMA, Salt Lake City, UT, USA). A nose piece with a spray tip is fitted to a standard syringe. The liquid drug to be delivered is first drawn into the syringe and then the spray tip is fitted onto the syringe. Another suitable device is a pre-filled device based on the same principle that is capable of delivering one or two doses (ACCUSPRAY™, Becton Dickinson Technologies, Research Triangle Park, NC, USA). The device of the present disclosure may alternatively comprise a traditional, simple metered-dose spray pumps require priming and some degree of overfill to maintain dose conformity for the labeled number of doses. These devises are well suited for drugs to be administered daily over a prolonged duration.

EMBODIMENTS OF THE DISCLOSURE

In a first embodiment, the present disclosure provides a composition comprising: about 1% w/v to about 15% w/v of olanzapine or a pharmaceutically acceptable salt thereof; about 0.1% w/v to about 1% w/v of dodecyl maltoside; about 30% w/v to about 40% w/v of N,N-dimethylacetamide; and about 40% w/v to about 70% w/v of polyethylene glycol, wherein the composition is a non-aqueous solution comprising less than about 3% w/v of water or less than about 1% w/v of water.

The first embodiment optionally includes one or more of the following Elements.

Element 1: The composition of the first embodiment, comprising about 2.5% w/v to about 12% w/v of the olanzapine or a pharmaceutically acceptable salt thereof.

Element 2: The composition of the first embodiment, comprising about 0.20% w/v to about 0.50% w/v of the dodecyl maltoside and optionally comprising Element 1.

Element 3: The composition of the first embodiment, comprising about 34% w/v to about 38% w/v of the N,N-dimethylacetamide and optionally comprising Element 1 or Element 2.

Element 4: The composition of the first embodiment, wherein the polyethylene glycol has an average molecular weight of about 200 Da to about 1000 Da, and optionally comprising one or more of Elements 1-3.

Element 5: The composition of the first embodiment, wherein the polyethylene glycol has an average molecular weight of about 600 Da, and optionally comprising one or more of Elements 1-4.

Element 6: The composition of the first embodiment, comprising about 44% w/v to about 66% w/v of the polyethylene glycol, and optionally comprising one or more of Elements 1-5.

Element 7: The composition of the first embodiments, wherein the ratio of the polyethylene glycol to the N,N-dimethylacetamide is from about 4:1 to about 1:4, and optionally comprising one or more of Elements 1-6.

Element 8: The composition of the first embodiment, wherein the ratio of the polyethylene glycol to the N,N-dimethylacetamide is about 3:2 and optionally comprising one or more of Elements 1-7.

Element 9: The composition of the first embodiment, wherein the amount of olanzapine is about 2.5 mg to about 10 mg or a pharmaceutically acceptable salt thereof, and optionally comprising one or more of Elements 1-8.

Element 10: The composition of the first embodiment, wherein the composition comprises less than 0.1% w/v of water, and optionally comprising one or more of Elements 1-9.

Element 11: The composition of the first embodiment, comprising about 2.5% w/v to about 12% w/v of the olanzapine or a therapeutically equivalent amount of an olanzapine salt, about 0.20% w/v to about 0.50% w/v of the dodecyl maltoside, about 34% w/v to about 38% w/v of the N,N-dimethylacetamide, and about 44% w/v to about 66% w/v of the polyethylene glycol, and optionally comprising one or more of Elements 1-10.

In a second embodiment, the present disclosure provides a single-use spray device comprising the composition according to Embodiment 1, optionally in combination with one or more of Elements 1-11, configured to discharge a volume of the composition that corresponds to 2.5 mg olanzapine to 15 mg of olanzapine upon actuation of the device.

In a third embodiment, the present disclosure provides a metered-multiple use spray device comprising the composition according to Embodiment 1, optionally in combination with one or more of Elements 111, configured to discharge a volume of the composition that corresponds to 2.5 mg olanzapine to 15 mg of olanzapine upon actuation of the device.

In a fourth embodiment, the present disclosure provides a method of treating acute agitation associated with one or more of schizophrenia, schizoaffective disorder, and bipolar disorder in a subject in need thereof comprising intranasally administering a composition comprising about 1 mg to about 15 mg of olanzapine or a therapeutically equivalent amount of an olanzapine salt, about 0.1 mg to about 1 mg dodecyl maltoside, about 30 mg to about 40 mg N,N-dimethylacetamide, and about 40 mg to about 70 mg of polyethylene glycol to a nasal mucosal membrane of the subject, wherein the composition is a non-aqueous solution comprising less than about 3% w/v of water.

Optionally, the method of the fourth embodiment further includes Element 10: a reduction of the severity of the acute agitation in the subject within about 20 minutes after administration.

In a fifth embodiment, the present disclosure provides a method of treating depression associated with bipolar disorder comprising intranasally administering a composition comprising about 1 mg to about 15 mg of olanzapine or a therapeutically equivalent amount of an olanzapine salt, about 0.1 mg to about 1 mg dodecyl maltoside, about 30 mg to about 40 mg N,N-dimethylacetamide, and about 40 mg to about 70 mg of polyethylene glycol to a nasal mucosal membrane of the subject, wherein the composition is a non-aqueous solution comprising less than about 3% w/v of water.

In a sixth embodiment, the present disclosure provides a method of treating mania associated with bipolar disorder comprising intranasally administering a composition comprising about 1% w/v to about 15% w/v of olanzapine or a therapeutically acceptable salt thereof, about 0.1% w/v to about 1% w/v dodecyl maltoside, about 30% w/v to about 40% w/v N,N-dimethylacetamide, and about 40% w/v to about 70% w/v of polyethylene glycol to a nasal mucosal membrane of the subject, wherein the composition is a non-aqueous solution comprising less than about 3% w/v of water.

In a seventh embodiment, the present disclosure provides a method of treating a mixed episode associated with bipolar disorder comprising intranasally administering a composition comprising about 1% w/v to about 15% w/v of olanzapine or a therapeutically equivalent amount of an olanzapine salt, about 0.1% w/v to about 1% w/v dodecyl maltoside, about 30% w/v to about 40% w/v N,N-dimethylacetamide, and about 40% w/v to about 70% w/v of polyethylene glycol to a nasal mucosal membrane of the subject, wherein the composition is a non-aqueous solution comprising less than about 3% w/v of water.

Any one of the fourth, fifth, sixth, or seventh embodiments may optionally include one or more of the following Elements:

Element 12: The method of any one of the fourth through seventh embodiments, wherein the composition comprises about 2.5% w/v to about 12% w/v of the olanzapine or equivalent amount of a salt thereof, optionally further including Element 11.

Element 13: The method of any one of the fourth through seventh embodiments, wherein the composition comprises about 2.5% w/v to about 10% w/v of the olanzapine or equivalent amount of a salt thereof, and optionally further comprising Element 11 and/or Element 12.

Element 14: The method of any one of the fourth through seventh embodiments, wherein the composition comprises about 0.20% w/v to about 0.50% w/v of the dodecyl maltoside, and optionally further comprising one or more of Elements 11-13.

Element 15: The method of any one of the fourth through seventh embodiments, wherein the composition comprises about 34% w/v to about 38% w/v of the N,N-dimethylacetamide, and optionally further comprising one or more of Elements 11-14.

Element 16: The method of any one of the fourth through seventh embodiments, wherein the polyethylene glycol has an average molecular weight of about 200 Da to about 1000 Da, and optionally further comprising one or more of Elements 11-15.

Element 17: The method of any one of the fourth through seventh embodiments, wherein the composition comprises about 44% w/v to about 66% w/v of the polyethylene glycol, and optionally further comprising one or more of Elements 11-16.

Element 18: The method of any one of the fourth through seventh embodiments, wherein the composition comprises about 2.5 mg to about 12 mg of the olanzapine or a therapeutically equivalent amount of an olanzapine salt, about 0.20 mg to about 0.50 mg dodecyl maltoside, about 34 mg to about 38 mg of the N,N-dimethylacetamide, and about 44 mg to about 66 mg of polyethylene glycol, and optionally further comprising one or more of Elements 11-17.

Element 19: The method of any one of the fourth through seventh embodiments, wherein the composition is provided in a pre-primed single use dosing device containing about 75 μL to about 200 μL of the composition, and optionally further comprising one or more of Elements 11-18.

Element 20: The method of any one of the fourth through seventh embodiments, wherein said administering comprises administering about 75 μL to about 200 μL of the composition to each nostril of the subject, and optionally further comprising one or more of Elements 11-19.

Element 21: The method of any one of the fourth through seventh embodiments, wherein the depression, mania, or mixed episodes manifest as recurring episodes and wherein one or more of the frequency, length, and severity of the recurring episodes is reduced, and optionally further comprising one or more of Elements 11-20

Element 22: The method of any one of the fourth through seventh embodiments, wherein after said administering, the subject is less likely to discontinue use of said composition in comparison to the likelihood of discontinuing use of an olanzapine composition administered intramuscularly or orally, and optionally further comprising one or more of Elements 11-21.

Element 23: The method of any one of the fourth through seventh embodiments, wherein the composition comprises less than about 1% w/v of water, and optionally further comprising one or more of Elements 11-22.

Element 24: The method of any one of the fourth through seventh embodiments wherein the ratio of the polyethylene glycol to the N,N-dimethylacetamide is from about 4:1 to about 1:4, and optionally further comprising one or more of Elements 11-23.

Element 25: The method of any one of the fourth through seventh embodiments wherein the ratio of the polyethylene glycol to the N,N-dimethylacetamide is about 3:2 and optionally further comprising one or more of Elements 11-24.

EXAMPLES

Example 1: Formulations

Various non-limiting examples of intranasal olanzapine compositions, as described herein, are provided in Table 2 below. Formulations represent 2.5 mg, 5.0 mg, 7.5 mg, 10 mg, 11 mg, 12 mg, and 15 mg olanzapine. In any case, the % w/w may be calculated by dividing the amount of components in mg by the total number of mg in the composition (e.g., 105 mg). For example, a composition comprising 2.5 mg olanzapine would comprise about 2.38% w/w olanzapine. Similarly, 12 mg olanzapine corresponds to 11.43% w/w olanzapine. In any embodiment, the olanzapine may be present as a salt (e.g., dicarboxylic acid salt such as tartrate), a solvate (e.g., hydrate), a solvate, polymorph, a cocrystal, in a complex or any combination thereof. In any embodiment, a formulation may comprise any amount of olanzapine including amounts between those listed in Table 2. A composition may comprise about 0.25 mg to about 0.5 mg dodecyl maltoside, a constant amount of DMA (37.80 mg), and QS to 105 mg with PEG-600. In any embodiment, a formulation may comprise any amount of dodecyl maltoside, DMA, or PEG-600 including amounts between those listed in Table 2. Notably, all compositions are solutions formulated without water and are non-aqueous. Each of these formulations yields a solution that is approximately 100 μL, and therefore each value also represents the weight by volume amount.

TABLE 2

| Component | \multicolumn{14}{c}{Formulation No.} |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| olanzapine (mg) | 2.5 | 2.5 | 5.0 | 5.0 | 7.50 | 7.50 | 10.0 | 10.0 | 11.0 | 11.0 | 12.0 | 12.0 | 15.0 | 15.0 |
| dodecyl maltoside (mg) | 0.25 | 0.50 | 0.25 | 0.50 | 0.50 | 0.25 | 0.25 | 0.50 | 0.25 | 0.50 | 0.25 | 0.50 | 0.25 | 0.50 |
| DMA (mg) | 37.80 | 37.80 | 37.80 | 37.80 | 37.80 | 37.80 | 37.80 | 37.80 | 37.80 | 37.80 | 37.80 | 37.80 | 37.80 | 37.80 |
| PEG600 (mg) | 64.45 | 64.2 | 61.95 | 61.70 | 59.2 | 59.45 | 56.95 | 56.70 | 55.95 | 55.70 | 54.95 | 54.70 | 51.95 | 51.70 |
| Total (mg)* | 105 | 105 | 105 | 105 | 105 | 105 | 105 | 105 | 105 | 105 | 105 | 105 | 105 | 105 |

*compositions are based on a theoretical specific gravity of 1.05

Example 2: Formulation Development

The formulation development strategy was predicated on the need to develop a formulation that has appropriate quality characteristics for nasal delivery of a therapeutic dose in a convenient single-dose delivery configuration with high patient acceptability and ease of use for either self-administration or care giver administration. On this premise an initial Quality Target Product Profile (QTPP) was developed (Table 2).

TABLE 3

| QTPP Element | Target | Requirement |
|---|---|---|
| Dosage form/route of administration | Nasal spray | High bioavailability, no first pass metabolism<br>High patient compliance<br>Ease of administration by patient/caregiver<br>More convenient than current product (IM) |
| Dosage design | Non-aqueous solution incorporating an absorption enhancer | Adequate drug stability over shelf-life<br>Adequate drug load and rapid absorption<br>Appropriate volume for nasal administration |
| Dose strengths (Proposed commercial strengths) | 5.0 mg, 7.5 mg, and 10 mg per 100 µL | Dose range to be efficacious and safe in the patient population |
| Stability | 24 months at room temperature | Commercially viable shelf-life<br>Patients able to carry product with them for convenience |
| Quality attributes | Identification<br>Appearance<br>Assay<br>Related substances<br>Intravail A3 content<br>Particulate matter<br>Moisture content<br>Fill volume/net content<br>Microbiological quality<br>Container closure integrity<br>Spray content uniformity<br>Droplet size distribution<br>Spray pattern/plume geometry | Must meet the appropriate compendial, ICH, or other applicable quality standards for a nasal product |
| Container closure system | Container closure suitable for the drug product in terms of compatibility over shelf-life and shipping | Container closure maintains its integrity over shelf-life<br>Minimal interactions with formulation |
| Clinically relevant nonmedical ingredients | Contains Intravail A3 | Permeation enhancer to improve rate and extent of drug absorption |

Elements of a potential delivery system (sprayer) are important to the QTPP, in addition to those detailed in Table 3. The combination product quality attributes are described in Table 4.

TABLE 4

| QTPP Element | Target | Requirement |
|---|---|---|
| Patient compliance and compatibility | Easy and convenient to use, non-invasive | Convenient to use<br>Portable<br>Non-invasive |
| Ease of use in patient population | Easy to follow IFU included | Easy self-medication or administration by caregiver |
| Reproducible dosing | Meets acceptance criteria for all pump performance criteria | Consistent dosing under typical patient-use circumstances |
| Adequate product shelf-life | At least 24 months shelf-life at room temperature | Commercially viable shelf-life Ability for patients to carry product with them for convenience |
| Portable and convenient to use | Small enough for a pocket or purse<br>No specialized storage required<br>Robust | To ensure patient compliance and medication always on hand |
| Compatible with the drug product formulation over shelf-life | Minimal component induced degradation or leachables of concern | Maintain product quality over shelf-life |
| Robust for shipment and day-to-day use purposes | Reliability >99.9% | Ensure consistent performance in commercial environment |
| Container closure integrity to avoid leaks | No leakage over shelf-life | Ensure full dose available Prevention of ingress of contaminants |

Table 4 summarizes the quality attributes of the drug product and details which attributes were classified as drug product critical quality attributes (CQAs). For the product, appearance, olanzapine assay and related substances, Intra-vail A3 assay, particulate matter, moisture, and microbial quality were identified as the subset of CQAs that could be impacted by the raw materials and processing and were therefore assessed in the initial formulation development studies. For the initial studies, the focus was primarily on appearance, olanzapine assay and related substances as these attributes informed selection of the solvent system. Microbiological quality was assumed to be a low risk at this stage due to the non-aqueous composition of the formulation and the low residual moisture level.

The combination product CQAs such as pump performance parameters (pump delivery, spray content uniformity, droplet size distribution and plume geometry/spray pattern) and container closure integrity were not formally assessed during the initial phase. The use of a commercial device with a proven track record provided a high level of assurance that these elements would not be problematic to the development program. Compatibility with the closure was informally assessed and shown not to be a concern.

TABLE 4

| Quality Attribute of Drug Product | Target | Justification |
|---|---|---|
| Appearance | Clear, yellow to amber liquid, free of visible particulate matter | Color change would be indicative of formulation degradation. Particulates would be indicative of degradation and precipitation or possible morphology changes producing crystallization. |
| Olanzapine assay | 90.0%-110.0% label claim | Assay decrease would be indicative of active degradation. |
| Olanzapine related substances | Olanzapine Related Compound B: NMT 1.5%<br>Olanzapine Related Compound C: NMT 1.5%<br>Individual Unidentified Impurities: NMT 1.5%<br>Total Impurities NMT 4.0% | Related substances increases would be indicative of active degradation and may be excipient related. |
| Intravail A3 assay | 90.0%-110.0% label claim | Assay decrease would be indicative of degradation. |
| Moisture | No specific target | Active is known to be sensitive to hydrolytic oxidation. |

As summarized above, the primary aim of the initial formulation development program was to achieve adequate solubility and stability of the drug substance in an acceptable solvent system that allowed administration of a full dose in a single 100 μL actuation. Olanzapine has poor aqueous stability and solubility. Some basic olanzapine physico-chemical parameters include: BCS Class 2, solubility of 0.02 mg/mL in water at pH 6.8, solubility of 0.034 mg/mL in water at 37° C., and pKa 4.01, 7.24. To achieve the highest required dose, a concentration of 100 mg/mL would be required and so an aqueous based system would not meet some key QTPP attributes.

Thus, non-aqueous systems were explored. Solvent selection was limited to pharmaceutically acceptable excipients listed on the FDA Inactive Ingredient Database (IID), under-standing that the solvent levels in the olanzapine formulations described herein would likely be higher than the amounts listed as safe. Evidence of safety for the solvents at the proposed levels in the olanzapine nasal sprays, taking into consideration the context of use (e.g., patient population, dosage, and duration of exposure), was therefore established. To support formulation assessment, stability indicating methods were reviewed in the literature and a method selected to provide an assessment of key degradants.

As a starting point, the non-aqueous solvents from an approved intranasal formulation were tested. Specifically, Vitamin E, benzyl alcohol and ethanol were assessed. It was apparent after two weeks at 40° C. that significant incompatibilities existed between olanzapine and the individual solvents, as indicated by increases in degradation products and color changes. The importance of the presence of oxygen to the degradation was investigated using nitrogen head spacing and found to have little impact on stability for this formulation series.

Other solvents including cottonseed oil, eucalyptol, polysorbate 20, polysorbate 80, trolamine, sesame oil, benzyl benzoate, cyclodextrin, and sterile water for injection were also tested and resulted in poor solubility, poor stability, or a combination thereof. Several of these solvents were also tested with micro milled olanzapine which also resulted in poor solubility, poor stability, or a combination thereof.

A broad screening approach was then performed with a range of solvents including oils, glycols, nonionic surfactants, and terpenoids, both with and without nitrogen head spacing. After one week at 40° C., related substances ranged from 1% to 12%, with the results varying significantly across the solvents and the glycols showing the most promise. In general, nitrogen head spacing did not provide significant improvement, even though the main degradants were oxidative degradation products. In addition to polyethylene glycol, dimethylacetamide exhibited good stability during the initial screen. It should also be noted that several of the solvents assessed (including the PEGs) did not have sufficient solubilizing capabilities to achieve the QTPP solubility criteria.

Dimethylacetamide and PEG 400 were next assessed individually at approximately 5 mg/mL over a two-month period at 40° C. The concentrations were relatively low versus the high target of 100 mg/mL due to the poorer solubilizing capacity of the PEG. The stability results were encouraging for both solvents in that USP Related Compounds B and C, the main hydrolysis/oxidative degradation products, did not significantly increase relative to the previous solvent systems studied. Dimethylacetamide had better stability characteristics than PEG 400. Based on these data a further series of experiments was initiated that included evaluation of a dimethylacetamide/PEG 200 binary solvent system for viscosity, and olanzapine solubility and stability.

Figure 2:
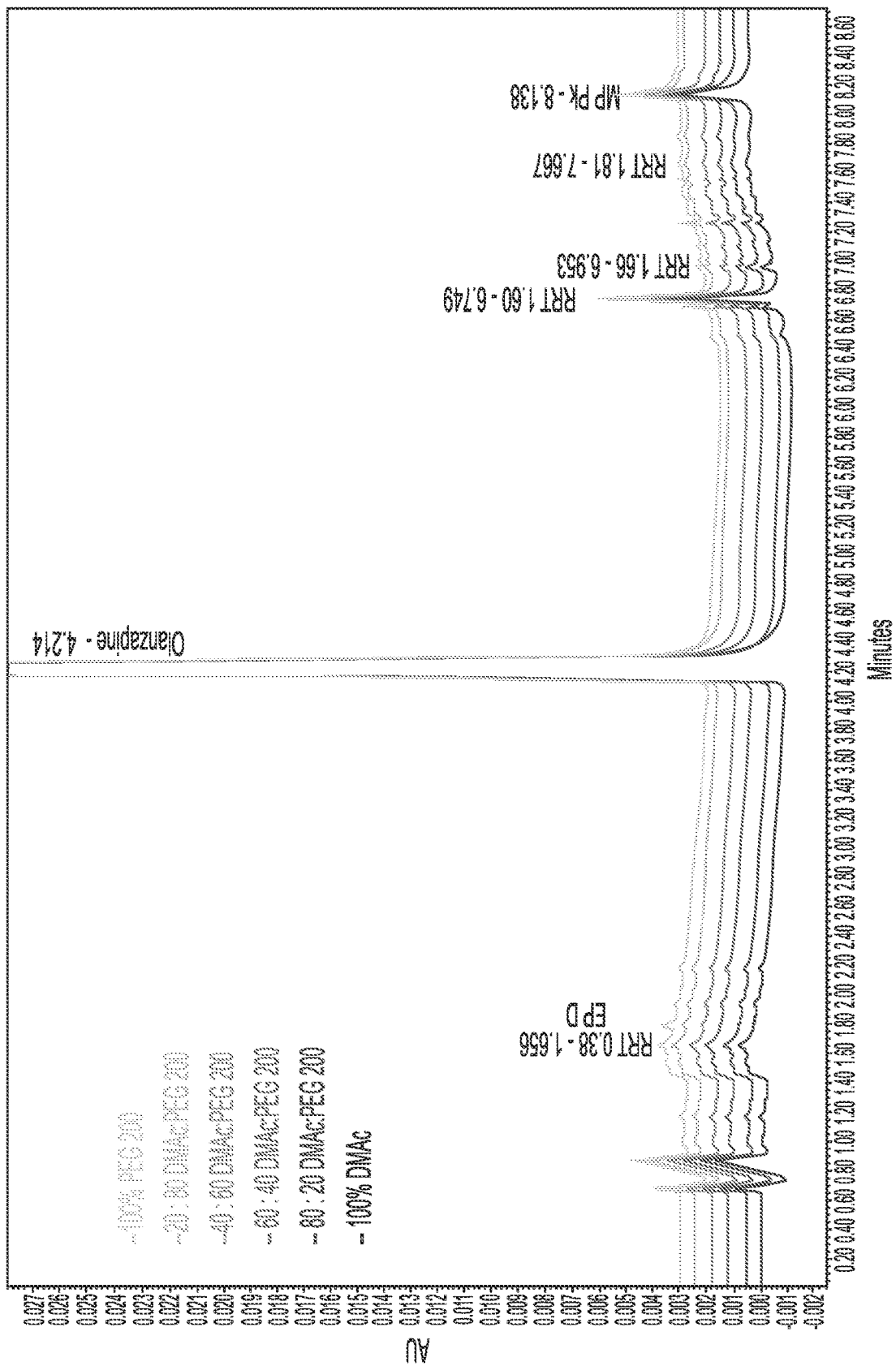
FIG. 2 depicts an overlay of chromatograms from a solubility study.

The solubility profile of olanzapine in PEG 200/dimethylacetamide was investigated as a first step to determine an appropriate binary composition range for further formulation development. Excess olanzapine was added to the solutions, stirred overnight, filtered, and assayed. The data from these experiments are tabulated in Table 5 and presented graphically in FIG. 1. The impurity profiles were also compared, and the chromatograms are provided in FIG. 2.

TABLE 5

| Solvent Composition | Olanzapine concentration (mg/g) | Appearance |
|---|---|---|
| 100% PEG 200 | 51.4 | Clear amber solution |
| 20% Dimethylacetamide/ 80% PEG 200 | 81.3 | Clear amber solution |
| 40% Dimethylacetamide/ 60% PEG 200 | 126.1 | Clear amber solution |
| 60% Dimethylacetamide/ 40% PEG 200 | 189.5 | Clear dark amber solution |
| 80% Dimethylacetamide/ 20% PEG 200 | 252.7 | Clear dark amber solution |
| 100% Dimethylacetamide | 341.7 | Clear dark amber solution |

Based on the solubility and stability data and the need for a highest concentration of at least 100 mg/mL, it was determined that a robust formulation would be achievable with compositions containing greater than approximately 40% dimethylacetamide. It was noted that USP Olanzapine Related Compound C (EP Impurity D) was detected in solutions containing higher amounts of PEG 200, which also supported increasing the dimethylacetamide levels.

A supplementary freeze-thaw experiment was performed with 180 mg/g solutions in 60/40 dimethylacetamide/PEG 200, 80/20 dimethylacetamide/PEG 200, and 100% dimethylacetamide. The solutions were subjected to five freeze-thaw cycles to confirm formulation robustness. There were no changes in appearance, confirming no potential for crystallization from freezing/crystal seeding etc.

The viscosity of the three formulations was also determined. The values ranged from 1.9 cP (100% dimethylacetamide) to 8.3 cP (60/40 dimethylacetamide/PEG 200).

At this point, it was concluded that a formulation consisting of a binary mixture of PEG and dimethylacetamide may be viable for further development. Adequate solubility had been demonstrated and viscosity was acceptable (although an increase was desired to increase residence time in the nose following administration), but further work on stability and the impact of PEG content was required.

Figure 3:
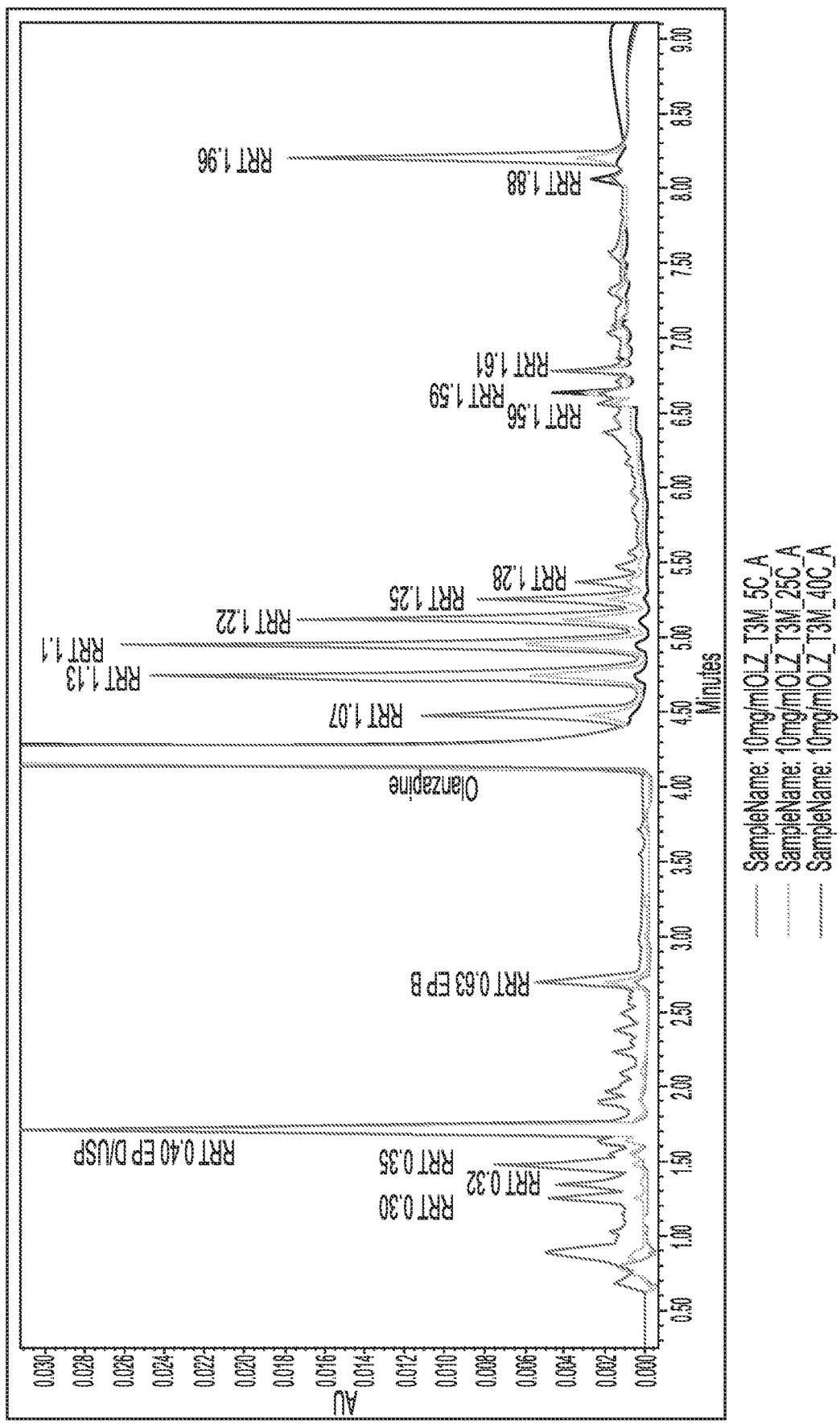
FIG. 3 depicts overlaid chromatograms for 10 mg/mL olanzapine in 100% PEG 200
Figure 4:
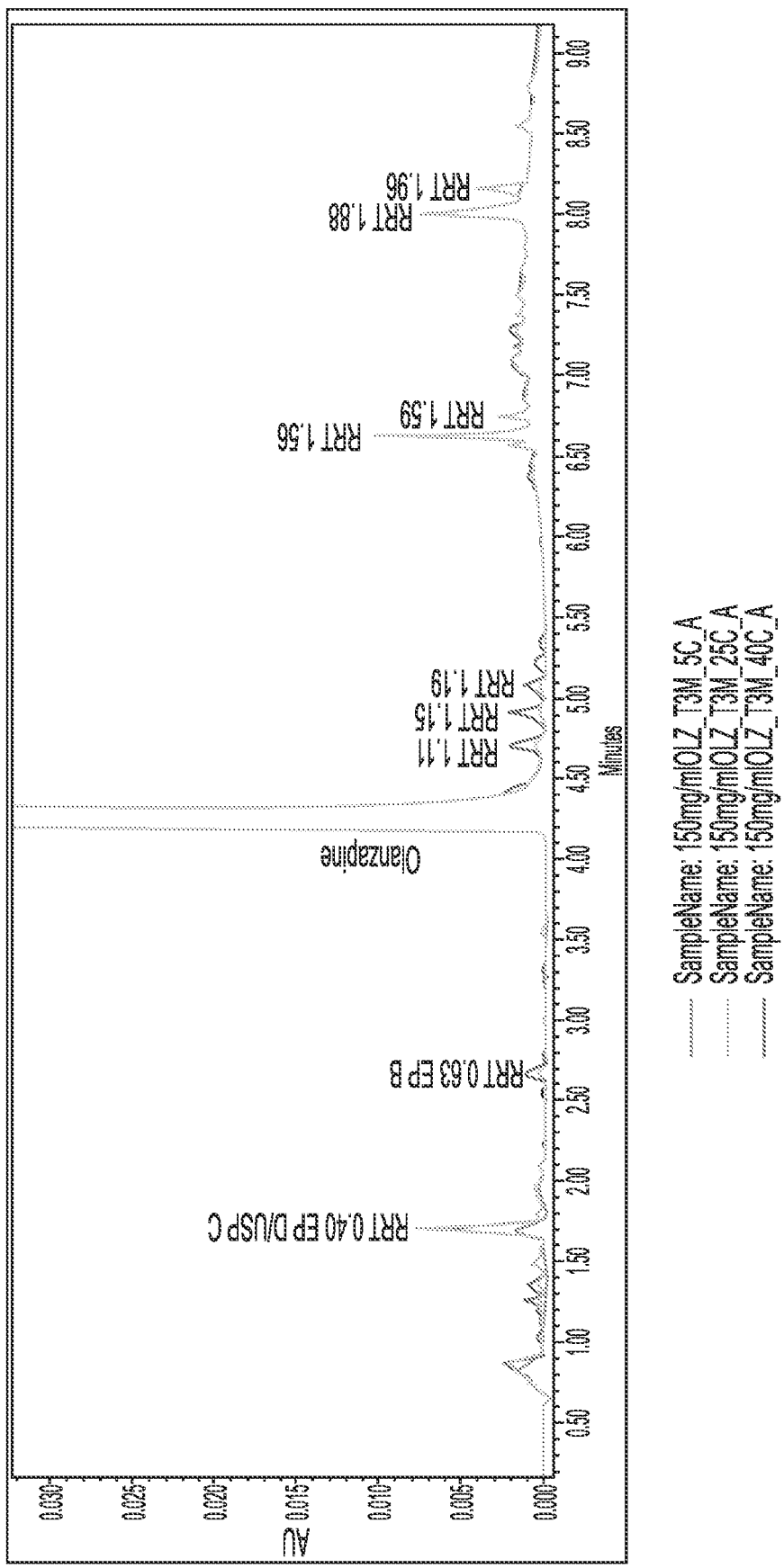
FIG. 4 depicts overlaid chromatograms for 150 mg/mL olanzapine in 50/50 dimethylacetamide/PEG 200.

A new stability study was initiated with two formulations: 150 mg/mL olanzapine in 50/50 dimethylacetamide/PEG 200 and 10 mg/mL olanzapine in PEG 200. Appearance, assay and related substances were monitored over a three-month period with samples stored at 5° C., 25° C./60% relative humidity (RH) and 40° C./75% RH for both formulations. The 50/50 dimethylacetamide/PEG 200 formulation was also evaluated at six months. The data are summarized in Table 6 and overlays of the three-month chromatograms are provided in FIG. 3 and FIG. 4.

TABLE 6

| 10 mg/mL Olanzapine in 100% PEG 200 | | | | | |
|---|---|---|---|---|---|
| Test | Condition | T-0 | T-1 month | T-3 month | T-6 month |
| Appearance | 5° C. | Clear yellow solution | NT | Clear light yellow solution | NT |
| | 25° C./60% RH | | NT | Clear light amber solution | NT |

TABLE 6-continued

|  |  | T-0 | T-1 month | T-3 month | T-6 month |
|---|---|---|---|---|---|
|  | 40° C./75% RH |  | Clear light amber solution | Clear amber solution | NT |
| Assay | 5° C. | 97.2% | NT | 96.2% | NT |
|  | 25° C./60% RH |  | NT | 94.6% | NT |
|  | 40° C./75% RH |  | 91.9% | 83.4% | NT |
| Related substances | 5° C. | USP RC 0.21%<br>RRT 1.60 0.12%<br>RRT 1.63 0.39%<br>Total 0.72% | NT | USP RC 1.1%<br>RRT 1.59 0.14%<br>RRT 1.60 ND<br>RRT 1.61 0.10%<br>RRT 1.63 ND<br>Total 1.3% | NT |
|  | 25° C./60% RH |  | NT | USP RC 1.5%<br>USP RB 0.13%<br>RRT 1.07 0.28%<br>RRT 1.13 0.40%<br>RRT 1.19 0.40%<br>RRT 1.22 0.25%<br>RRT 1.25 0.10%<br>RRT 1.60 ND<br>RRT 1.61 0.11%<br>RRT 1.63 ND<br>RRT 1.96 0.14%<br>Total 3.3% | NT |
|  | 40° C./75% RH |  | USP RC 1.71%<br>USP RB 0.16%<br>RRT 1.05 0.18%<br>RRT 1.11 0.54%<br>RRT 1.16 0.56%<br>RRT 1.20 0.35%<br>RRT 1.23 0.16%<br>RRT 1.52 0.46%<br>RRT 1.55 0.61%<br>RRT 1.58 0.11%<br>RRT 1.70 0.13%<br>RRT 1.85 0.22%<br>RRT 1.88 0.29%<br>Total 5.5% | RRT 0.30 0.17%<br>RRT 0.32 0.19%<br>RRT 0.35 0.35%<br>USP RC 2.2%<br>RRT 0.45 0.10%<br>USP RB 0.32%<br>RRT 1.07 0.80%<br>RRT 1.13 1.60%<br>RRT 1.19 1.64%<br>RRT 1.22 1.03%<br>RRT 1.25 0.46%<br>RRT 1.28 0.16%<br>RRT 1.52 ND<br>RRT 1.55 ND<br>RRT 1.58 ND<br>RRT 1.61 0.13%<br>RRT 1.70 ND<br>RRT 1.85 ND<br>RRT 1.96 0.86%<br>Total 10.0% | NT |

| 150 mg/mL Olanzapine in 50/50 Dimethylacetamide/PEG 200 | | | | | |
|---|---|---|---|---|---|
|  |  | T-0 | T-1 month | T-3 month | T-6 month |
| Appearance | 5° C. | Clear amber solution | NT | Clear amber solution | Clear amber solution |
|  | 25° C./60% RH |  | NT | Clear dark amber solution | Clear dark amber solution |
|  | 40° C./75% RH |  | Clear dark amber solution | Clear dark brown solution | Clear black solution |
| Assay | 5° | 100.6% | NT | 97.9% | 99.4% |
|  | 25° C./60% RH |  | NT | 96.6% | 97.4% |
|  | 40° C./75% RH |  | 97.5% | 95.8% | 95.9% |
| Related substances | 5° C. | RRT 1.63 0.39%<br>Total 0.39% | NT | USP RC 0.11%<br>RRT 1.56 0.33%<br>RRT 1.63 ND<br>RRT 1.88 0.34%<br>Total 0.79% | USP RC 0.10%<br>RRT 1.56 ND<br>RRT 1.61 0.11%<br>RRT 1.63 ND<br>RRT 1.88 ND<br>RRT 2.22 0.19%<br>Total 0.40% |
|  | 25° C./60% RH |  | NT | USP RC 0.38%<br>RRT 1.56 0.31%<br>RRT 1.63 ND<br>RRT 1.88 0.31%<br>RRT 1.96 0.15%<br>Total 1.2% | USP RC 0.41%<br>RRT 1.07 0.16%<br>RRT 1.13 0.11%<br>RRT 1.56 ND<br>RRT 1.61 0.12%<br>RRT 1.63 ND<br>RRT 1.88 ND<br>RRT 1.92 0.14%<br>Total 0.93% |

TABLE 6-continued

| 40° C./75% RH | USP RC 0.49%<br>RRT 1.55 0.70%<br>RRT 1.58 ND<br>RRT 1.85 0.42%<br>RRT 1.88 0.20%<br>Total 1.8% | USP RC 0.34%<br>RRT 1.11 0.18%<br>RRT 1.15 0.15%<br>RRT 1.56 0.29%<br>RRT 1.58 ND<br>RRT 1.88 0.27%<br>RRT 1.96 0.14%<br>Total 1.4% | USP RC 0.17%<br>RRT 1.07 0.26%<br>RRT 1.13 0.35%<br>RRT 1.17 0.33%<br>RRT 1.21 0.20%<br>RRT 1.56 ND<br>RRT 1.58 ND<br>RRT 1.61 0.12%<br>RRT 1.88 ND<br>RRT 1.96 ND<br>Total 1.4% |
|---|---|---|---|

Several conclusions were drawn from this data: Results show degradation in both samples, but most significantly in the 10 mg/mL olanzapine in PEG 200 sample; Temperature was a significant factor for overall formulation stability; A series of peaks characteristic of a polymer are seen in both samples, suggesting reaction of the olanzapine with different polymer chains or potential polymer degradation itself; these peaks are most prevalent in the 10 mg/mL formulation in 100% PEG 200.

These data indicated a stable formulation may be possible, but PEG content (and grade) would need to be further optimized to maximize product stability.

As a first step, solubility was assessed for mixtures of dimethylacetamide and different molecular weight grades of PEG, which had two potential benefits. First, higher molecular weight PEGs would impart a higher viscosity to the final formulation, potentially enhancing nasal residence time. Second, the higher molecular weight polymer would have fewer residual hydroxyl groups, thereby minimizing the suspected drug-excipient interaction observed with PEG 200. PEG 600 and PEG 1000 were selected for this screen as they are significantly higher molecular weight than the PEG 200 used to date, with 3 to 5 times fewer hydroxyl groups and higher viscosities. Higher molecular weight PEGs (>1000) were excluded because of their poorer miscibility with dimethylacetamide (e.g., PEG 3350 was insoluble in 60-90% dimethylacetamide) and the need to add heat to aid dissolution (PEG 600 melts in the range 15-25° C., PEG 1000 in the range 37-40° C. and PEG 3350 in the range 50-54° C.). A summary of the solubility data is provided in Table 7.

TABLE 7

| PEG Molecular Weight | Dimethylacetamide/PEG Ratio | Olanzapine Solubility (mg/mL) |
|---|---|---|
| 600 | 60/40 | 199 |
| 1000 | 60/40 | 217 |
| 600 | 30/70 | 108 |
| 1000 | 30/70 | PEG insoluble |
| 600 | 10/90 | 59 |
| 1000 | 10/90 | PEG insoluble |

The data show that adequate olanzapine solubility is achieved with PEG 600 content as low as 40% and is also above the highest target concentration of 100 mg/mL in 70% PEG 600 and 30% dimethylacetamide. PEG 1000 was soluble in dimethylacetamide at 40% but did not dissolve at higher levels.

Based on this information, PEG 600 was selected for further evaluation. As a first step a range of formulations were prepared containing olanzapine and Intravail A3. The formulations were assessed for dissolution and freeze-thaw characteristics. The compositions of the formulations are detailed in Table 8 and the results of the dissolution and freeze-thaw study in Table 9.

TABLE 9

| | Composition (Ratio PEG/DMA)* | | | | |
|---|---|---|---|---|---|
| | Form. A<br>80/20 | Form. B<br>60/40 | Form. C<br>40/60 | Form. D<br>20/80 | Form. E<br>0/100 |
| Olanzapine | 12 g | 12 g | 12 g | 12 g | 12 g |
| Intravail A3 | 0.25 mg | 0.25 mg | 0.25 mg | 0.25 mg | 0.25 mg |
| PEG 600 | 70 g | 53 g | 35 g | 18 g | 0 |
| Dimethylacetamide | 18 g | 35 g | 53 g | 70 g | 100 g |

*Solvent ratios are based on weight and calculated using PEG density of 1.15 and dimethylacetamide density of 0.94.

TABLE 9

| | Composition (Ratio PEG/DMA) | | | | |
|---|---|---|---|---|---|
| | Form. A<br>80/20 | Form. B<br>60/40 | Form. C<br>40/60 | Form. D<br>20/80 | Form. E<br>100 |
| Dissolution observations | Suspension formed. After 2 hours dissolution incomplete. | All formed clear amber solutions within first hour of mixing. Allowed to sit for one hour post stirring. No separation or precipitation observed. | | | |

TABLE 9-continued

| | Composition (Ratio PEG/DMA) | | | | |
|---|---|---|---|---|---|
| | Form. A 80/20 | Form. B 60/40 | Form. C 40/60 | Form. D 20/80 | Form. E 100 |
| Freeze-thaw observations | Completely solid post freezing. Melting took approximately 2 hours. Undissolved material remained. | Completely solid post freezing. Melting took approximately 45 minutes. No separation or precipitation observed. | Thick gel, mostly solid post freezing. Melting took approximately 30 minutes. No separation or precipitation observed. | Completely liquid. No separation or precipitation observed. | Completely liquid. No separation or precipitation observed. |

These data narrowed the formulation range to a maximum PEG 600 content of 60%. A three-month stability study at −20° C., 25° C./60% RH, and 40° C./75% RH was then performed. Formulations B through E were placed on stability, along with a formulation equivalent to Formulation B but prepared with PEG 200 instead of PEG 600 to allow a direct comparison between PEG grades. Evaluation of Formulation B and Formulation E was extended to include a 6-month and a 12-month time point at 40° C./75% RH and 25° C./60% RH. The data are presented in Table 10 through Table 14.

At the initiation of the stability study, analytical method qualification had not been completed. For the initial time point (T-0), the related substances values were high as a consequence of sample degradation post preparation and prior to analysis. The method was subsequently modified to address this issue, which explains the high initial related substances data (particularly peaks at RRT 1.61 and RRT 1.76) at T-0 relative to the later time points.

TABLE 10

| 120 mg/mL Olanzapine in 60/40 PEG 200: Dimethylacetamide | | | | |
|---|---|---|---|---|
| Test | Condition | T-0 | T-1 month | T-3 month |
| Appearance | −20° C. | Clear dark yellow solution | Clear light amber solution with precipitation | Clear light amber solution with precipitation |
| | 25° C./60% RH | | Clear light amber solution | Clear amber solution |
| | 40° C./75% RH | | Clear dark amber solution | Clear dark amber solution |
| Assay | −20° C. | 98.5% | NT | NT |
| | 25° C./60% RH | | 97.5% | 97.3% |
| | 40° C./75% RH | | 96.1% | 96.4% |
| Related substances | −20° C. | RRT 1.11: 0.15% RRT 1.61: 0.65% RRT 1.76: 0.55% Total: 1.4% | NT | NT |
| | 25° C./60% RH | | USP RC: 0.17% RRT 1.11: 0.11% RRT 1.61: ND RRT 1.76: ND Total: 0.28% | RRT 0.38: 0.12% USP RC: 0.20% RRT 1.11: ND RRT 1.13: 0.11% RRT 1.17: 0.07% RRT 1.55: 0.12% RRT 1.61: ND RRT 1.76: ND RRT 1.80: 0.14% RRT 1.82: 0.19% RRT 1.86: 0.07% Total: 1.0% |
| | 40° C./75% RH | | USP RC: 0.46% RRT 1.11: 0.14% RRT 1.61: ND RRT 1.76: ND RRT 1.82: 0.20% Total: 0.81% | RRT 0.38: 0.10% USP RC: 0.15% USP RB: 0.08% RRT 1.11: 0.34% RRT 1.13: 0.34% RRT 1.17: 0.30% RRT 1.21: 0.19% RRT 1.23: 0.09% RRT 1.55: 0.16% RRT 1.61: ND RRT 1.76: ND RRT 1.80: 0.16% RRT 1.82: 0.17% RRT 1.86: 0.06% Total: 2.1% |

TABLE 10-continued

120 mg/mL Olanzapine in 60/40 PEG 200: Dimethylacetamide

| Test | Condition | T-0 | T-1 month | T-3 month |
|---|---|---|---|---|
| Intravail assay | −20° C. | 98.8% | NT | NT |
|  | 25° C./60% RH |  | NT | NT |
|  | 40° C./75% RH |  | NT | 109.0% |
| Viscosity | −20° C. | <20 cP | NT | NT |
|  | 25° C./60% RH |  | NT | <20 cP |
|  | 40° C./75% RH |  | NT | NT |

ND = not detected;
NT = not tested;
RRT = relative retention time;
USP RB = USP olanzapine related compound B;
USP RC = USP olanzapine related compound C

TABLE 11

120 mg/mL Olanzapine in 60/40 PEG 600: Dimethylacetamide

| Test | Condition | T-0 | T-1 month | T-3 month | T-6 month | T-12 month |
|---|---|---|---|---|---|---|
| Appearance | −20° C. | Clear dark yellow solution | Clear light amber solution | Clear light amber solution | Clear light amber solution | Clear amber solution |
|  | 25° C./60% RH |  | Clear light amber solution | Clear dark amber solution | Clear dark amber solution | Clear dark amber solution |
|  | 40° C./75% RH |  | Clear dark amber solution | Clear dark amber solution | Clear dark amber solution | Clear dark amber solution |
| Assay | −20° C. | 98.5% | NT | NT | NT | NT |
|  | 25° C./60% RH |  | 98.7% | 98.5% | 99.7% | 97.1% |
|  | 40° C./75% RH |  | 97.1% | 97.9% | 98.6% | 94.7% |
| Related substances | −20° C. | RRT 1.11: 0.17% RRT 1.55: 0.10% RRT 1.61: 0.70% RRT 1.76: 0.60% Total: 1.6% | NT | NT | NT | NT |
|  | 25° C./60% RH |  | USP RC: 0.11% RRT 1.11: ND RRT 1.55: BLQ RRT 1.61: ND RRT 1.76: ND RRT 1.82: 0.10% Total: 0.21% | RRT 0.38: 0.15% USP RC: 0.18% RRT 1.11: ND RRT 1.55: 0.14% RRT 1.61: ND RRT 1.76: ND RRT 1.80: 0.15% RRT 1.82: 0.29% RRT 1.86: 0.07% Total: 0.99% | RRT 0.38: 0.15% USP RC: 0.21% RRT 1.11: ND RRT 1.55: ND RRT 1.61: ND RRT 1.76: ND RRT 1.80: BLQ RRT 1.82: 0.31% RRT 1.86: ND Total: 0.67% | RRT 0.38: ND USP RC: 0.23% RRT 1.11: ND RRT 1.55: ND RRT 1.61: BLQ RRT 1.76: ND RRT 1.80: ND RRT 1.82: ND RRT 1.86: ND Total: 0.23% |
|  | 40° C./75% RH |  | USP RC: 0.28% RRT 1.11: ND RRT 1.55: BLQ RRT 1.61: ND RRT 1.76: ND RRT 1.82: 0.22% Total: 0.50% | RRT 0.38: USP RC: 0.13% RRT 1.11: ND RRT 1.55: 0.18% RRT 1.61: ND RRT 1.76: ND RRT 1.80: 0.19% RRT 1.82: 0.26% RRT 1.86: 0.06% Total: 0.95% | RRT 0.38: USP RC: BLQ RRT 1.11: ND RRT 1.13: 0.11% RRT 1.41: 0.24% RRT 1.55: ND RRT 1.61: ND RRT 1.76: ND RRT 1.80: BLQ RRT 1.82: 0.23% RRT 1.86: ND Total: 0.71% | RRT 0.38: ND USP RC: ND RRT 1.11: ND RRT 1.13: ND RRT 1.41: 0.58% RRT 1.55: ND RRT 1.61: BLQ RRT 1.76: BLQ RRT 1.80: ND RRT 1.82: ND RRT 1.86: ND Total: 0.58% |
| Intravail assay | −20° C. | 101.2% | NT | NT | NT | NT |
|  | 25° C./60% RH |  | NT | NT | 100.9% | NT |
|  | 40° C./75% RH |  | NT | 106.3% | 102.7% | NT |
| Viscosity | −20° C. | 23.9 cP | NT | NT | NT | NT |
|  | 25° C./60% RH |  | NT | 23.8 cP | 24.4 cP | NT |
|  | 40° C./75% RH |  | NT | NT | NT | NT |

BLQ = below level of quantitation (0.1%);
ND = not detected;
NT = not tested;
RRT = relative retention time;
USP RB = USP olanzapine related compound B;
USP RC = USP olanzapine related compound C

TABLE 12

120 mg/mL Olanzapine in 40/60 PEG 600: Dimethylacetamide

| Test | Condition | T-0 | T-1 month | T-3 month |
|---|---|---|---|---|
| Appearance | −20° C. | Clear dark yellow solution | Clear light amber solution | Clear light amber solution |
|  | 25° C./60% RH |  | Clear light amber solution | Clear dark amber solution |
|  | 40° C./75% RH |  | Clear dark amber solution | Clear dark amber solution |
| Assay | −20° C. | 99.8% | NT | NT |
|  | 25° C./60% RH |  | 98.0% | 97.7% |
|  | 40° C./75% RH |  | 96.1% | 96.4% |
| Related substances | −20° C. | RRT 1.11: 0.16% | NT | NT |
|  | 25° C./60% RH | RRT 1.55: 0.41%<br>RRT 1.61: 0.72%<br>RRT 1.76: 0.62%<br>Total: 1.9% | USP RC: 0.11%<br>RRT 1.11: ND<br>RRT 1.55: BLQ<br>RRT 1.61: ND<br>RRT 1.76: ND<br>RRT 1.82: 0.15%<br>Total: 0.26% | RRT 0.38: 0.12%<br>USP RC: 0.14%<br>RRT 1.11: ND<br>RRT 1.55: 0.15%<br>RRT 1.61: ND<br>RRT 1.76: ND<br>RRT 1.80: 0.16%<br>RRT 1.82: 0.29%<br>RRT 1.86: 0.07%<br>Total: 0.91% |
|  | 40° C./75% RH |  | USP RC: 0.21%<br>RRT 1.11: ND<br>RRT 1.55: BLQ<br>RRT 1.61: ND<br>RRT 1.76: ND<br>RRT 1.82: 0.19%<br>Total: 0.40% | RRT 0.38: 0.07%<br>USP RC: 0.05%<br>RRT 1.11: ND<br>RRT 1.55: 0.18%<br>RRT 1.61: ND<br>RRT 1.76: ND<br>RRT 1.80: 0.18%<br>RRT 1.82: 0.23%<br>RRT 1.86: 0.05%<br>Total: 0.76% |
| Intravail assay | −20° C. | 103.0% | NT | NT |
|  | 25° C./60% RH |  | NT | NT |
|  | 40° C./75% RH |  | NT | 104.8% |
| Viscosity | −20° C. | <20 cP | NT | NT |
|  | 25° C./60% RH |  | NT | <20 cP |
|  | 40° C./75% RH |  | NT | NT |

BLQ = below level of quantitation (0.1%);
ND = not detected;
NT = not tested;
RRT = relative retention time;
USP RB = USP olanzapine related compound B;
USP RC = USP olanzapine related compound C

TABLE 13

120 mg/mL Olanzapine in 20/80 PEG 600: Dimethylacetamide

| Test | Condition | T-0 | T-1 month | T-3 month |
|---|---|---|---|---|
| Appearance | −20° C. | Clear dark yellow solution | Clear light amber solution | Clear light amber solution |
|  | 25° C./60% RH |  | Clear light amber solution | Clear dark amber solution |
|  | 40° C./75% RH |  | Clear dark amber solution | Clear dark amber solution |
| Assay | −20° C. | 99.0% | NT | NT |
|  | 25° C./60% RH |  | 98.2% | 99.0% |
|  | 40° C./75% RH |  | 97.4% | 98.0% |
| Related substances | −20° C. | RRT 1.11: 0.16% | NT | NT |
|  | 25° C./60% RH | RRT 1.61: 0.79%<br>RRT 1.76: 0.68%<br>Total: 1.6% | RRT 1.11: ND<br>RRT 1.61: ND<br>RRT 1.76: ND<br>RRT 1.82: 0.14%<br>Total: 0.14% | RRT 0.38: 0.07%<br>USP RC: 0.11%<br>RRT 1.11: ND<br>RRT 1.55: 0.17%<br>RRT 1.61: ND<br>RRT 1.76: ND<br>RRT 1.80: 0.17%<br>RRT 1.82: 0.24%<br>RRT 1.86: 0.07%<br>Total: 0.82% |
|  | 40° C./75% RH |  | USP RC: 0.19%<br>RRT 1.11: ND<br>RRT 1.61: ND | RRT 0.38: 0.07%<br>USP RC: BLQ<br>USP RB: 0.06% |

TABLE 13-continued

| | 120 mg/mL Olanzapine in 20/80 PEG 600: Dimethylacetamide | | | |
|---|---|---|---|---|
| Test | Condition | T-0 | T-1 month | T-3 month |
| | | | RRT 1.76: ND | RRT 1.11: ND |
| | | | RRT 1.82: 0.15% | RRT 1.55: 0.19% |
| | | | Total: 0.34% | RRT 1.61: ND |
| | | | | RRT 1.76: ND |
| | | | | RRT 1.80: 0.19% |
| | | | | RRT 1.82: 0.20% |
| | | | | RRT 1.86: 0.05% |
| | | | | Total: 0.75% |
| Intravail assay | −20° C. | 104.4% | NT | NT |
| | 25° C./60% RH | | NT | NT |
| | 40° C./75% RH | | NT | 107.2% |
| Viscosity | −20° C. | <20 cP | NT | NT |
| | 25° C./60% RH | | NT | <20 cP |
| | 40° C./75% RH | | NT | NT |

BLQ = below level of quantitation (0.1%);

ND = not detected;

NT = not tested;

RRT = relative retention time;

USP RB = USP olanzapine related compound B;

USP RC = USP olanzapine related compound C

TABLE 14

| | 120 mg/mL Olanzapine in Dimethylacetamide | | | | | |
|---|---|---|---|---|---|---|
| Test | Condition | T-0 | T-1 month | T-3 month | T-6 month | T-12 month |
| Appearance | −20° C. | Clear dark yellow solution | Clear light amber solution | Clear light amber solution | Clear light amber solution | Clear amber solution |
| | 25° C./60% RH | | Clear light amber solution | Clear dark amber solution | Clear dark amber solution | Clear dark amber solution |
| | 40° C./75% RH | | Clear dark amber solution | Clear dark amber solution | Clear dark amber solution | Clear dark amber solution |
| Assay | −20° C. | 100.3% | NT | NT | NT | NT |
| | 25° C./60% RH | | 99.2% | 99.1% | 99.4% | 97.6% |
| | 40° C./75% RH | | 97.7% | 98.7% | 100.3% | 97.7% |
| Related substances | −20° C. | RRT 1.11: 0.19% | NT | NT | NT | NT |
| | 25° C./60% RH | RRT 1.61: 0.83% | RRT 1.11: ND | RRT 0.38 0.07% | RRT 0.38: BLQ | RRT 0.38: ND |
| | | RRT 1.76: ND | RRT 1.61: ND | USP RC: 0.12% | USP RC: 0.17% | USP RC: BLQ |
| | | RRT 1.76: 0.72% | RRT 1.76: ND | RRT 0.47: 0.06% | RRT 0.47: ND | RRT 0.47: ND |
| | | Total: 1.7% | Total: ND | RRT 1.11: ND | RRT 1.11: ND | RRT 1.11: ND |
| | | | | RRT 1.13: 0.13% | RRT 1.13: ND | RRT 1.13: ND |
| | | | | RRT 1.55: 0.18% | RRT 1.55: ND | RRT 1.55: ND |
| | | | | RRT 1.61: ND | RRT 1.61: ND | RRT 1.61: BLQ |
| | | | | RRT 1.76: ND | RRT 1.76: ND | RRT 1.76: ND |
| | | | | RRT 1.80: 0.18% | RRT 1.80: BLQ | RRT 1.80: ND |
| | | | | RRT 1.82: 0.19% | RRT 1.82: 0.17% | RRT 1.82: ND |
| | | | | RRT 1.86: 0.07% | RRT 1.86: ND | RRT 1.86: ND |
| | | | | Total: 1.0% | Total: 0.34% | Total: ND |

TABLE 14-continued 120 mg/mL Olanzapine in Dimethylacetamide

| Test | Condition | T-0 | T-1 month | T-3 month | T-6 month | T-12 month |
|---|---|---|---|---|---|---|
| | 40° C./75% RH | | USP RC: 0.18% | RRT 0.30: 0.05% | RRT 0.30: BLQ | RRT 0.30: ND |
| | | | RRT 1.11: ND | RRT 0.38: 0.05% | RRT 0.38: BLQ | RRT 0.38: ND |
| | | | RRT 1.61: ND | USP RC: BLQ | USP RC: BLQ | USP RC: BLQ |
| | | | RRT 1.76: ND | USP RB: 0.09% | USP RB: 0.11% | USP RB: 0.10% |
| | | | RRT 1.82: 0.12% | RRT 1.11: ND | RRT 1.11: ND | RRT 1.11: ND |
| | | | Total: 0.29% | RRT 1.55 0.19% | RRT 1.13 0.20% | RRT 1.55: ND |
| | | | | RRT 1.61: ND | RRT 1.55: ND | RRT 1.61: BLQ |
| | | | | RRT 1.76: ND | RRT 1.61: ND | RRT 1.76: ND |
| | | | | RRT 1.80: 0.19% | RRT 1.76: ND | RRT 1.80: ND |
| | | | | RRT 1.82: 0.14% | RRT 1.80: BLQ | RRT 1.82: ND |
| | | | | Total: 0.72% | RRT 1.82: 0.12% | Total: 0.10% |
| | | | | | Total: 0.43% | |
| Intravail assay | −20° C. | 105.1% | NT | NT | NT | NT |
| | 25° C./60% RH | | NT | NT | NT | NT |
| | 40° C./75% RH | | NT | 106.6% | NT | NT |
| Viscosity | −20° C. | <20 cP | NT | NT | NT | NT |
| | 25° C./60% RH | | NT | <20 cP | NT | NT |
| | 40° C./75% RH | | NT | NT | NT | NT |

BLQ = below level of quantitation (0.1%);
ND = not detected;
NT = not tested;
RRT = relative retention time;
USP RB = USP olanzapine related compound B;
USP RC = USP olanzapine related compound C Overall, these initial data demonstrate that the products maintain their quality characteristics for the duration of the study. PEG 600 showed improved compatibility relative to PEG 200 and there was a slight improvement in stability with respect to related substances as the level of PEG 600 decreased. However, the 12-month and 6-month data for 120 mg/mL olanzapine in 60:40 PEG 600: dimethylacetamide at 25° C./60% RH and 40° C./75% RH, respectively, demonstrate the product has satisfactory quality characteristics. It is noted that there appears to be a decrease in some individual related substances at the 6- and 12-month time points. This may be due to secondary degradation of these related substances, although at this stage of development no formal studies have been initiated. The darkening of the solution is due to minor increases in degradation products. The degradant at RRT 1.82 has a significant absorption in the visible spectrum and is likely the main cause of the color change. Other characteristics remain unchanged. Based on the stability data, the formulation using a 60:40 PEG 600: dimethylacetamide ratio was selected for further development.

The drug product is a true solution and therefore olanzapine solubility in the solvent system is a key physicochemical parameter to ensure it remains in solution and can be delivered reproducibly in terms of dose and spray characteristics.

The olanzapine used to date has been of a defined polymorph and formulation studies performed have identified a solvent composition that has excess solubilizing capacity above the target highest concentration of 100 mg/mL. In addition, formulation freeze-thaw studies have demonstrated the robustness of the formulation with respect to temperature fluctuations.

Example 3: A Pilot, Phase 1, Single-Dose, Open-Label, Randomized, Parallel Group Study to Characterize the Pharmacokinetics, Safety, and Tolerability of Intramuscular and Intranasal Formulations of Olanzapine in Healthy Male Subjects The primary objective of this study is to characterize the pharmacokinetic (PK) profiles of olanzapine after single dose administration of 7.5 mg via intramuscular (IM) injection (Zyprexa), 7.5 mg solution with 0.25% Intravail® A3 absorption enhancer via nasal spray (NRL-4A), and 7.5 mg solution with 0.50% Intravail A3 absorption enhancer via nasal spray (NRL-4B) in healthy male subjects. The secondary objective is to evaluate the safety and tolerability of olanzapine administered as a single dose of 7.5 mg with 0.25% Intravail absorption enhancer nasal spray solution (NRL-4A) and as a single dose of 7.5 mg with 0.50% Intravail absorption enhancer nasal spray solution (NRL-4B) in healthy male subjects compared with a single dose administration of 7.5 mg olanzapine via IM injection (Zyprexa). Pharmacological treatments often used during acute episodes of agitation include benzodiazepines and antipsychotics delivered either by IM or intravenous route to facilitate rapid drug action. However, these administrations can result in injury to staff and/or subject, especially if the subject is agitated, and is often perceived as humiliating. Moreover, administration requires trained health care workers, and their use is limited to clinics, emergency rooms, hospitals, or psychiatric units.

Intranasal (IN) drug delivery is a preferable alternative as it is a practical, noninvasive dosing option that is convenient for self-administration or administration by health care providers or family members. It provides rapid onset (potentially equivalent to IM), is not subject to first pass metabolism, and has good bioavailability, potentially resulting in a better safety profile by reducing dose-related side effects. An agitated, usually psychotic, subject living alone may not be able to wait a few hours for a therapeutic effect of an oral formulation or make the trip to the emergency room or health center for an IM injection, wherein a ready to use IN formulation is convenient to carry and administer, making it an attractive option in any social setting in addition to the emergency room or health center.

This is a pilot phase 1, open-label, randomized, parallel group clinical study designed to compare the PK, safety, and tolerability of IM (Zyprexa) and IN (NRL-4A and NRL-4B) formulations of olanzapine in healthy male subjects.

The study will comprise of Screening followed by Baseline and an Open-Label Treatment Period. Subjects will be admitted to a Clinical Research Unit (CRU) at Day −1 (the day before dosing) to undergo assessments to reconfirm their eligibility to enter the study. Subjects will stay in the CRU until after the postdose assessments and samples collection on Day 4. The time that a subject is discharged from the CRU may be agreed with the unit staff, but subjects must return for all designated PK samples and on scheduled times for observation.

Approximately 24 healthy male subjects, aged between 18 and 55 years (both inclusive), will be randomized in a 1:1:1 ratio and divided into 3 treatment groups and receive a single dose of olanzapine, either by intramuscular (IM) injection (olanzapine 7.5 mg via IM injection (Zyprexa)) or one of two intranasal formulations while reclined, remaining reclined for up to 2 hours. Subjects are instructed to drink at least 8 oz. of fluid prior to administration. Intranasal formulations are formulations 5 and 6 in Table 2-7.5 mg olanzapine+0.25 mg dodecyl maltoside or 7.5 mg olanzapine+0.50 mg dodecyl maltoside. Safety assessments are performed after each administration and include physical examination, vital sign measurements (e.g., blood pressure, heart rate), ECGs, and clinical laboratory tests. Self-reported incidences of lightheadedness or dizziness are noted. Objective evaluation of nasal irritation is assessed after each intranasal administration using a 6-point (0-5) score. The scoring is done by a trained observer based on an assessment of the nasal mucosa prior to dosing (baseline) and at 30 (±5 min) minutes, and 1 (±10 min), 2 (±15 min), 4 (±30 min), 6 (±30 min), 8 (±30 min), and 24 (±30 min) hours post dose. Irritation is assessed by evaluating the degree of mucosal inflammation and bleeding. The subjects are required to report any incident of bleeding or inflammation in-between the actual evaluation time points.

Blood pressure (BP) and pulse are measured after each administration of study drug. BP and pulse are taken at baseline, pre-dose, and at 15 (±2 min), 30 (±2 min), and 45 (±5 min) minutes, and 1 (±5 min), 1.25 (±5 min), 1.5 (±5 min), 1.75 (±5 min), 2 (±5 min), 2.5 (±10 min), 3 (±10 min), 3.5 (±10 min), 4 (±10 min), 8 (±10 min), 12 (±10 min) and 24 (±10 min) hours post dose. BP and pulse are collected while sitting and after the subject has been standing for 3 minutes. Subjects are also questioned by a trained observer regarding any feelings of lightheadedness or dizziness.

Injection site reactions are assessed after each IM administration using a 6-point (0-5) score. The scoring is done by a trained observer based on an assessment of the IM injection site prior to dosing (baseline), and at 30 (±5 min) minutes, and 1 (±10 min), 2 (±15 min), 4 (±30 min), 6 (±30 min), 8 (±30 min), and 24 (±30 min) hours post dose. The subjects are required to report any incident of injection site reaction in-between the actual evaluation time points.

Objective evaluations of pain will be assessed using a 11-point Numeric Rating Scale (NRS; 0 through 10), where 0 means "no pain" and 10 means "worst pain imaginable." Pain scores will be reported by the subject just prior to dosing (baseline) and at 15 (±2 min) and 30 (±5 min) minutes, and 1 (±10 min), 2 (±15 min), 4 (±30 min), 6 (±30 min) and 8 (±30 min) hours post dosing.

Objective evaluations of sedation are made using a 6-point (0 through 5) sedation scoring system to assess the degree of drowsiness of the subjects after each administration of study drug. Sedation scores are reported by the subject (if awake) as well as by a trained observer, using the same rating scale, just prior to dosing (baseline) and at 15 (±2 min) and 30 (±5 min) minutes, and 1 (±10 min), 2 (±15 min), 4 (±30 min), 6 (±30 min) and 8 (±30 min) hours post dose. Subjects are also questioned by the trained observer regarding their degree of drowsiness.

Blood samples for the measurement of plasma concentrations of olanzapine are collected before (0, pre-dosing), at 5, 10, 15, 30, and 45 minutes, and 1, 1.25, 1.5, 1.75, 2, 4, 8, 12, 24, 36, 48, 72, 96, 144, 192, and 240 hours after dosing. Actual blood collection times may vary as follows: 1) ±1 minute for the 5- and 10-minute samples, 2) ±2 minutes for the 15- to 60-minute samples, 3) ±5 minutes for the 1.25- to 8-hour samples, 4) ±15 minutes for the 12- and 24-hour samples, 5) ±2 hours for the 36- and 48-hour samples, 6) ±6 hours for the 72- and 96-hour samples, and 7) ±24 hours for the 144, 192, and 240-hour samples.

The Columbia Suicide Severity Rating Scale (C-SSRS), a measure of suicidal ideation and behavior, is used to document suicidality in order to classify suicidal events using the Columbia Classification Algorithm of Suicide Assessment. Suicidality is assessed at screening, baseline, and prior to discharge from Clinical Research Unit.

Inclusion criteria includes (1) a body weight of 51 kg to 111 kg, and body mass index within the range of 18 to 35 kg/m$^2$ inclusive; (2) male subjects aged 18 to 55, inclusive; (3) no clinically significant abnormal findings in medical history, on physical examination, electrocardiogram (Corrected QT interval (QTcF) <450 milliseconds; or corrected QT interval <480 milliseconds in subjects with Bundle Branch Block, based on QTc values obtained over a brief recording period), or clinical laboratory results during screening (4) no clinically significant abnormalities (in the opinion of the investigator) as assessed by review of medical and surgical history, physical examination, vital sign measurements, ECG, and laboratory evaluations conducted at screening and CRU admission; (5) normal blood pressure (BP) (systolic BP 90 to 140 mmHg, inclusive, diastolic BP <90 mmHg) and pulse rate (50 to 100 beats/minute, inclusive). Exclusion criteria include (1) unstable disease conditions; any clinical or laboratory measurements assessed by the investigator as clinically relevant (including ECG, hematology, biochemistry and urine analysis, etc.); Current or previous history of clinically significant, as deemed by the investigator, cardiac, cardio- or cerebrovascular, respiratory, gastrointestinal, endocrine, hematologic, psychiatric (specifically schizophrenia, schizoaffective disorder, bipolar I or major depressive disorder), renal, hepatic, pulmonary, or nervous system diseases, use of drug that can change the absorption, metabolism or elimination of IP, or result in danger or other drugs or diseases that interfere with the interpretation of study data; (2) a history of seasonal or nonseasonal allergies, nasal polyps or any nasal passage abnormality that could interfere with nasal spray administration, or any other condition which, in the opinion of the investigator, may jeopardize the safety of the subject or impact the validity of the study results; (3) definite or suspected personal history or family history of adverse reactions or hypersensitivity to the IP or to drugs with a similar chemical structure (History of sensitivity to any of the IPs, or components thereof or a history of drug or other allergy that, in the opinion of the investigator or medical monitor, contraindicates their participation); (4) any clinically significant disease within 4 weeks prior to enrollment; (5) subjects with a lifetime history of alcohol or drug abuse or have tested positive for opiates, cocaine, benzodiazepines, barbiturates, or amphetamine, or have a history of illicit drug use (Intermittent use of cannabis, defined as greater than 1 use per week is permitted, but must not occur within 1 week prior to screening, and for the duration of the study); (6) significant traumatic injury, major surgery, or open biopsy within 30 days prior to screening; (7) history of major depression or suicide attempt; (8) judged by the investigator to be at significant risk for suicide, violence, or homicide (Suicide risk is defined as answering 'Yes' to items 4 or 5 on the Suicidal Ideation section of the Columbia-suicide severity rating scale (C-SSRS) at screening or has attempted suicide in the 18 months prior to screening); (9) history of postural orthostatic tachycardia syndrome or orthostatic hypotension upon standing during physical examination at screening; (10) history of allergic or adverse responses to olanzapine or any of the IP ingredients; (11) participation in a clinical trial within 30 days prior to the first dose of study drug (Participation in an observational (non-interventional) study is not excluded as long as there are no scheduling conflicts with this study); (12) taking over the counter products and natural health products (including herbal remedies, homeopathic and traditional medicines, probiotics, food supplements such as vitamins, minerals, amino acids, essential fatty acids, and protein supplements used in sports) within 14 days prior to IP administration, with the exception of the occasional use of paracetamol (up to 2 g daily); (13) inadequate or difficult venous access that may jeopardize the quality or timing of the PK samples; (14) a positive blood screen for HIV, Hepatitis B surface antigen (HbSAg), or Hepatitis C at screening or baseline; (15) a positive urine screen for alcohol, drugs of abuse (except for cannabis), or cotinine as screening or baseline; (16) subject is mentally or legally incapacitated; (17) unwillingness or inability to follow the procedures outlined in the protocol; (18) other conditions which, in the investigator's judgment, render subjects unsuitable for the clinical study.

Primary endpoints for this study will include plasma concentrations of olanzapine obtained from serial PK sampling after IM and IN administration; Maximum observed plasma concentration (Cmax); Time to maximum plasma concentration (tmax); Area under the concentration-time curve (AUC) from time zero to the last quantifiable concentration (AUC0-t) in plasma; AUC from time zero extrapolated to infinity (AUC0-∞), in plasma; Terminal elimination half-life (t1/2) of olanzapine in plasma; Terminal elimination rate constant ($\lambda z$); Apparent clearance (CL/F) of olanzapine in plasma uncorrected for bioavailability (F); Apparent volume of distribution during the terminal phase (Vz/F) of olanzapine in plasma.

Safety endpoints will include Incidence of AEs and serious AEs; Laboratory, vital signs, and ECG values; Concomitant medications; Assessment of psychiatric status using C-SSRS; Biometric assessments: Nasal irritation, sedation, and pain scoring.

The analysis populations will include the PK Full Population, PK Evaluable Population, and the Safety Population.

PK Full Population: All subjects who receive a known amount of IP and have at least one quantifiable concentration of olanzapine in plasma.

PK Evaluable Population: All subjects who receive a known amount of IP and have at least one estimable PK parameter.

Safety Population: All subjects who received any amount of IP. Safety Assessments:

Adverse events will be collected and reviewed to evaluate the safety and tolerability of olanzapine nasal spray solutions compared to IM injection. Other safety measures will include physical examination, vital sign measurements, ECGs, and clinical laboratory tests.

Blood pressure, pulse rate, body temperature, and respiratory rate will be measured at predose (Baseline), and at 15 (±2) minutes, 30 (±2) minutes, 45 (±5) minutes, 1 hour (±5 minutes), 1.25 hours (±5 minutes), 1.5 hours (±5 minutes), 1.75 hours (±5 minutes), 2 hours (±5 minutes), 2.5 hours (±10 minutes), 3 hours (±10 minutes), 3.5 hours (±10 minutes), 4 hours (±10 minutes), 8 hours (±10 minutes), 12 hours (±10 minutes), and 24 hours (±10 minutes) postdose. Measurements will be collected in supine position and after the subject has been standing for 3 minutes. Subjects will also be questioned by a trained observer regarding any feelings of lightheadedness or dizziness.

Objective evaluations of nasal irritation will be assessed after IN administration of IP (Arm 2 and Arm 3) using a 6-point (0 through 4) scoring system. The scoring will be done by a trained observer based on an assessment of the nasal mucosa predose (Baseline), and at 5 (±1) minutes, 10 (±2) minutes, 30 (±5) minutes, 1 hour (±10 minutes), 2 hours (±15 minutes), 4 hours (±30 minutes), 6 hours (±30 minutes), 8 hours (±30 minutes), and 24 hours (±30 minutes) postdose, and on Day 14 (end of study). The subjects will also be required to report any incident of bleeding or inflammation in-between the actual evaluation time points.

Objective evaluations of sedation will be made using a 6-point (0 through 5) sedation scoring system to assess the degree of drowsiness of the subjects after administration of IP. Sedation scores will be reported by the subject (if awake) as well as by a trained observer, using the same rating scale, just prior to dosing (Baseline) and at 15 (±2) minutes, 30 (±5) minutes, 1 hour (±10 minutes), 2 hours (±15 minutes), 4 hours (±30 minutes), 6 hours (±30 minutes), and 8 hours (±30 minutes) postdose. Subjects will also be questioned by the trained observer regarding their degree of drowsiness.

Objective evaluations of pain will be assessed using a 11-point NRS (0 through 10), where 0 means "no pain" and 10 means "worst pain imaginable." Pain scores will be reported by the subject just prior to dosing (Baseline) and at 15 (±2) minutes, 30 (±5) minutes, 1 hour (±10 minutes), 2 hours (±15 minutes), 4 hours (±30 minutes), 6 hours (±30 minutes), and 8 hours (±30 minutes) postdose.

The C-SSRS, a measure of suicidal ideation and behavior, will be used to document suicidality in order to classify suicidal events using the Columbia Classification Algorithm of Suicide Assessment. Suicidality will be assessed at Screening, Baseline, and prior to discharge from CRU.

All safety assessments, demographic variables, and disposition data will be presented in subject data listings.

Descriptive statistics will be used to tabulate and summarize study outcomes. Background and demographic characteristics will be presented. Continuous variables will be summarized by descriptive statistics (sample size, mean, standard deviation, median, minimum, and maximum). Discrete variables will be summarized by frequencies and percentages. Table summaries will be presented by treatment and time point as applicable.

For purposes of the statistical presentations, treatment will be defined by the 3 treatment arms: Single dose administration of olanzapine 7.5 mg via IM injection (Zyprexa); single dose administration of olanzapine 7.5 mg solution with 0.25% Intravail A3 absorption enhancer via nasal spray; and single dose administration of olanzapine 7.5 mg solution with 0.50% Intravail A3 absorption enhancer via nasal spray.

Electrocardiograms, vital signs, and clinical laboratory tests data (observed and change from baseline) will be summarized by time point using appropriate descriptive statistics.

Shift from baseline tables will be presented for chemistry and hematology laboratory parameters. Any ECG abnormalities should be confirmed by a trained cardiologist.

Adverse events will be summarized by presenting the number and percentage of subjects having any adverse event. The number and percentage of subjects reporting a treatment-emergent AE will be tabulated by system organ class and preferred term (coded using Medical Dictionary for Regulatory Activities). Treatment-emergent AEs will be further classified by severity and relationship to treatment.

Safety measures for sedation will be summarized using frequency tables. Frequency tables will be used to summarize C-SSRS results as data permit.

Individual subject plasma concentrations, actual sampling times, and PK parameters will be listed by treatment. Descriptive statistics will be calculated by treatment for plasma concentrations and PK parameters. Individual subject and mean plasma concentrations will be graphically displayed on linear and semi-logarithmic axes.

The PK parameters Cmax, AUC0-t, AUC0-∞, for olanzapine will be compared among treatments using an analysis of variance (ANOVA) model with treatment as fixed effect using the natural logarithm of the PK parameter. For each PK parameter, confidence intervals (CI; 90%) will be constructed for the geometric mean ratios, olanzapine nasal (Test)-to-olanzapine IM (Reference) using the 2 one-sided t-test procedure. The point estimates and confidence limits will be exponentiated back to the original scale. Comparability between olanzapine nasal (Test) and olanzapine IM (Reference) will be assessed from the geometric mean ratios and 90% CI for each PK parameter response.

Approximately 24 healthy male subjects (8 subjects per treatment arm). An interim analysis is planned after 6 subjects per treatment arm have completed the observation period and PK results are available to determine if additional subjects may be required. The variance estimate obtained from the ANOVA model of the primary endpoint (AUC, Cmax) based on the first N=18 subjects will be used to check the power of the statistical test. Evidence of high variability in the PK parameters (coefficient of variation ≥30%) will suggest to enroll at least N=24 subjects as planned per protocol.

Each subject will participate in the study for up to 35 days, which comprises of a 21-day. Screening Period and a Treatment Period of 14 days, which includes a 4-day Confinement. Period in the CRU, and a 10-day Follow-up Period.

All publications mentioned herein are incorporated by reference in their entirety. Nothing herein is to be construed as an admission that the disclosure is not entitled to antedate such disclosure by virtue of prior disclosure.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the disclosure, in addition to those described herein, will be apparent to those skilled in the art from the foregoing description. Such modifications are also intended to fall within the scope of the appended claims.

The invention claimed is:

1. A composition comprising:
    about 1% w/v to about 15% w/v of olanzapine or a pharmaceutically acceptable salt thereof;
    about 0.1% w/v to about 1% w/v of dodecyl maltoside;
    about 30% w/v to about 40% w/v of N,N-dimethylacetamide; and
    about 40% w/v to about 70% w/v of polyethylene glycol, wherein the composition is a non-aqueous solution comprising less than about 3% w/v of water.

2. The composition of claim 1, comprising about 2.5% w/v to about 12% w/v of the olanzapine or a pharmaceutically acceptable salt thereof.

3. The composition of claim 1, comprising about 0.20% w/v to about 0.50% w/v of the dodecyl maltoside.

4. The composition of claim 1, comprising about 34% w/v to about 38% w/v of the N,N-dimethylacetamide.

5. The composition of claim 1, wherein the polyethylene glycol has an average molecular weight of about 200 Da to about 1000 Da.

6. The composition of claim 1, wherein the polyethylene glycol has an average molecular weight of about 600 Da.

7. The composition of claim 1, comprising about 44% w/v to about 66% w/v of the polyethylene glycol.

8. The composition of claim 1, wherein the amount of olanzapine is about 1 mg to about 15 mg or a pharmaceutically acceptable salt thereof.

9. The composition of claim 1, wherein the ratio of the polyethylene glycol to the N,N-dimethylacetamide is from about 4:1 to about 1:4.

10. The composition of claim 1, wherein the ratio of the polyethylene glycol to the N,N-dimethylacetamide is about 3:2.

11. The composition of claim 1, comprising about 2.5% w/v to about 12% w/v of the olanzapine or a pharmaceutically acceptable salt thereof, about 0.20% w/v to about 0.50% w/v of the dodecyl maltoside, about 34% w/v to about 38% w/v of the N,N-dimethylacetamide, and about 44% w/v to about 66% w/v of the polyethylene glycol.

12. The composition of claim 1, wherein the composition comprises less than 1% w/v of water.

13. The composition of claim 1, wherein the composition comprises less than about 0.1% w/v of water.

14. A single-use spray device comprising the composition according to claim 1, configured to discharge a volume of the composition that corresponds to 2.5 mg olanzapine to 15 mg of olanzapine upon actuation of the device.

15. A method of treating acute agitation associated with one or more of schizophrenia, schizoaffective disorder, and bipolar disorder in a subject in need thereof comprising intranasally administering a composition comprising about 1% w/v to about 15% w/v of olanzapine or a pharmaceutically acceptable salt thereof, about 0.1% w/v to about 1% w/v dodecyl maltoside, about 30% w/v to about 40% w/v N,N-dimethylacetamide, and about 40% w/v to about 70% w/v of polyethylene glycol to a nasal mucosal membrane of the subject, wherein the composition is a non-aqueous solution comprising less than about 3% w/v of water.

16. The method of claim 15, wherein the composition comprises about 1 mg to about 15 mg of the olanzapine or a pharmaceutically acceptable salt thereof.

17. The method of claim 15, wherein the composition comprises about 2.5 mg to about 10 mg of the olanzapine or a pharmaceutically acceptable salt thereof.

18. The method of claim 15, wherein the composition comprises about 0.20 mg to about 0.50 mg of the dodecyl maltoside.

19. The method of claim 15, wherein the composition comprises about 34% w/v to about 38% w/v of the N,N-dimethylacetamide.

20. The method of claim 15, wherein the polyethylene glycol has an average molecular weight of about 200 Da to about 1000 Da.

21. The method of claim 15, wherein the composition comprises about 44% w/v to about 66% w/v of the polyethylene glycol.

22. The method of claim 15, wherein the ratio of the polyethylene glycol to the N,N-dimethylacetamide is from about 4:1 to about 1:4.

23. The method of claim 15, wherein the ratio of the polyethylene glycol to the N,N-dimethylacetamide is about 3:2.

24. The method of claim 15, wherein the composition comprises about 2.5 mg to about 15 mg of the olanzapine or a pharmaceutically acceptable salt thereof, about 0.20% w/v to about 0.50% w/v dodecyl maltoside, about 34% w/v to about 38% w/v of the N,N-dimethylacetamide, and about 44% w/v to about 66% w/v of polyethylene glycol.

25. The method of claim 15, wherein the severity of the acute agitation in the subject is reduced within about 20 minutes after administration.

26. The method of claim 15, wherein the composition is provided in a pre-primed single use dosing device containing about 75 µL to about 200 µL of the composition.

27. The method of claim 15, wherein the composition is provided in a pre-primed single use dosing device containing about 100 µL of the composition.

28. The method of claim 15, wherein said administering comprises administering about 75 µL to about 200 µL of the composition to each nostril of the subject.

29. The method of claim 15, wherein said administering comprises administering about 100 µL of the composition to each nostril of the subject.

30. The method of claim 15, wherein the composition comprises less than 1% w/v of water.

* * * * *